(12) United States Patent
Won et al.

(10) Patent No.: US 11,827,742 B2
(45) Date of Patent: Nov. 28, 2023

(54) EPOXY COMPOUND, COMPOSITION PREPARED THEREFROM, SEMICONDUCTOR DEVICE PREPARED THEREFROM, ELECTRONIC DEVICE PREPARED THEREFROM, ARTICLE PREPARED THEREFROM, AND METHOD OF PREPARING ARTICLE

(71) Applicant: Samsung Electronics Co., Ltd., Suwon-si (KR)

(72) Inventors: Jonghoon Won, Yongin-si (KR); Dahye Park, Anyang-si (KR); Kyeong Pang, Suwon-si (KR); In Kim, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 46 days.

(21) Appl. No.: 17/404,480

(22) Filed: Aug. 17, 2021

(65) Prior Publication Data

US 2022/0056197 A1 Feb. 24, 2022

(30) Foreign Application Priority Data

Aug. 18, 2020 (KR) .................. 10-2020-0103436

(51) Int. Cl.
*C08G 59/26* (2006.01)
*C08G 59/62* (2006.01)
(Continued)

(52) U.S. Cl.
CPC ........... *C08G 59/26* (2013.01); *C08G 59/063* (2013.01); *C08G 59/621* (2013.01); *C08L 63/00* (2013.01);
(Continued)

(58) Field of Classification Search
CPC .... C08G 59/26; C08G 59/063; C08G 59/621; C08G 2190/00; C08L 63/00; C08L 2203/206
(Continued)

(56) References Cited

U.S. PATENT DOCUMENTS 5,290,887 A 3/1994 Hefner, Jr. et al.
5,387,657 A 2/1995 Hefner, Jr. et al.
(Continued)

FOREIGN PATENT DOCUMENTS

DE 04311967 A1 10/1994
EP 0578054 A 1/1994
(Continued)

OTHER PUBLICATIONS

Balamurugan Rathinam et al., "Synthesis and Properties of a Liquid Crystalline Thermoset Epoxy Resin Containing 1,3,4-Oxadiazole Groups," High Performance Polymers, GB, vol. 21, No. 3, pp. 251-264, 1999.

(Continued)

*Primary Examiner* — David T Karst
(74) *Attorney, Agent, or Firm* — CANTOR COLBURN LLP

(57) ABSTRACT

An epoxy compound including a 5-membered aromatic heterocyclic ring represented by Formula 1 or Formula 2, a composition prepared using the epoxy compound, a semiconductor device prepared using the epoxy compound, an electronic device prepared using the epoxy compound, an article prepared using the epoxy compound, and a method of preparing the article:

E1-(M1)$_{a1}$-(L1)$_{b1}$-M3-(L2)$_{b2}$-(M2)$_{a2}$-E2    Formula 1

E1-(M1)$_{a1}$-(L1)$_{b1}$-M3-(L2)$_{b2}$-(M2)$_{a2}$-(L5)$_{b5}$-A-(L6)$_{b6}$-(M4)$_{a3}$-(L3)$_{b3}$-M6-(L4)$_{b4}$-(M5)$_{a4}$-E2    Formula 2

(Continued)

wherein in Formulae 1 and 2, M1, M2, M3, M4, M5, M6, L1, L2, L3, L4, L5, L6, E1, E2, a1, a2, a3, a4, b1, b2, b3, b4, b5, and b6 are the same as those defined in the detailed description.

18 Claims, 4 Drawing Sheets

(51) Int. Cl.
   *C08L 63/00* (2006.01)
   *C08G 59/06* (2006.01)
(52) U.S. Cl.
   CPC .... *C08G 2190/00* (2013.01); *C08L 2203/206* (2013.01)
(58) Field of Classification Search
   USPC .......................................................... 528/96
   See application file for complete search history.

(56) References Cited

U.S. PATENT DOCUMENTS

| | | | |
|---|---|---|---|
| 5,441,668 A | 8/1995 | Hornung et al. | |
| 5,443,752 A | 8/1995 | Hornung | |
| 5,447,656 A | 9/1995 | Jungbauer et al. | |
| 5,876,628 A | 3/1999 | Illian et al. | |
| 7,425,354 B2 | 9/2008 | Yanai et al. | |
| 2005/0213009 A1* | 9/2005 | Yanai | C09K 19/32 349/137 |
| 2012/0316313 A1 | 12/2012 | Emrick et al. | |

FOREIGN PATENT DOCUMENTS

| | | |
|---|---|---|
| EP | 0620262 A2 | 10/1994 |
| JP | 2005171235 A | 6/2005 |
| JP | 5862479 B2 | 2/2016 |
| JP | 2006282531 A | 10/2019 |
| WO | 1994026720 A1 | 11/1994 |
| WO | 2006025611 A1 | 3/2006 |
| WO | 2019207081 A1 | 10/2019 |

OTHER PUBLICATIONS

Extended European Search Report dated Jan. 19, 2022, issued in EP Patent Application No. 21191661.4, 9 pp., 2022.
Korotkikh N. I. et al., "Synthesis of 1,3,4-Oxidiazole and Xanthen-2-One Luminophoric Epoxide Monomers," Chemistry of Heterocyclic Compounds, Springer US, New York, (Jan. 1, 1999), vol. 35, No. 3, pp. 358-362, XP008024157, 2009.
Ryu Beom-Young et al., "Bisphenol-1,2,3-triazole (BPT) Epoxies and Cyanate Esters: Synthesis and Self-Catalyzed Curing," Macromolecules, US, vol. 44, No. 14, pp. 5693-5700, XP055869831, 2011.
Beom-Young Ryu and Todd Emrick, Bisphenol-1,2,3-triazole (BPT) Epoxies and Cyanate Esters Synthesis and Self-Catalyzed Curing, Macromolecules 2011, 44, 14, 5693-5700.
English Abstract of JP2013032340, Feb. 14, 2013.

* cited by examiner

EPOXY COMPOUND, COMPOSITION PREPARED THEREFROM, SEMICONDUCTOR DEVICE PREPARED THEREFROM, ELECTRONIC DEVICE PREPARED THEREFROM, ARTICLE PREPARED THEREFROM, AND METHOD OF PREPARING ARTICLE

CROSS-REFERENCE TO RELATED APPLICATION

This application is based on and claims priority to Korean Patent Application No. 10-2020-0103436, filed on Aug. 18, 2020, in the Korean Intellectual Property Office, and all the benefits accruing therefrom under 35 U.S.C. § 119, the entire content of which is incorporated by reference herein.

BACKGROUND

1. Field

The present disclosure relates to an epoxy compound, a composition prepared using the epoxy compound, a semiconductor device prepared using the epoxy compound, an electronic device prepared using the epoxy compound, an article prepared using the epoxy compound, and a method of preparing the article.

2. Description of Related Art

Due to the trend of manufacturing semiconductor circuits having high complexity and high density, thermal stability of a molding material for releasing heat generated from the semiconductor circuits has become important.

An epoxy molding compound (EMC) including a thermosetting resin is used as a molding material of a semiconductor package.

An inorganic filler with high thermal conductivity is added to increase thermal conductivity of the EMC.

However, in spite of the addition of the high-thermal-conductivity inorganic filler, the increase in thermal conductivity of the EMC is insignificant.

SUMMARY

Provided is an epoxy compound providing improved heat release characteristics by having a novel structure.

Provided is an epoxy resin composition including the epoxy compound.

Provided is a semiconductor device including a cured product prepared using the composition.

Provided is an electronic device including a cured product prepared using the composition.

Provided is an article including a cured product prepared using the composition.

Provided is a method of preparing the article.

Additional aspects will be set forth in part in the description which follows and, in part, will be apparent from the description, or may be learned by practice of the presented embodiments of the disclosure.

According to an aspect of an embodiment, an epoxy compound including a 5-membered aromatic heterocyclic ring is represented by Formula 1 or Formula 2:

$$E1\text{-}(M1)_{a1}\text{-}(L1)_{b1}\text{-}M3\text{-}(L2)_{b2}\text{-}(M2)_{a2}\text{-}E2 \quad \text{Formula 1}$$

$$E1\text{-}(M1)_{a1}\text{-}(L1)_{b1}\text{-}M3\text{-}(L2)_{b2}\text{-}(M2)_{a2}\text{-}(L5)_{b5}\text{-}A\text{-}(L6)_{b6}\text{-}(M4)_{a3}\text{-}(L3)_{b3}\text{-}M6\text{-}(L4)_{b4}\text{-}(M5)_{a4}\text{-}E2 \quad \text{Formula 2}$$

In Formulae 1 and 2,

M1, M2, M4, and M5 are each independently an arylene group represented by Formulae 3a to 3e,

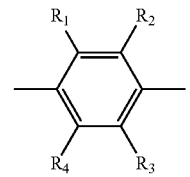

Formula 3a

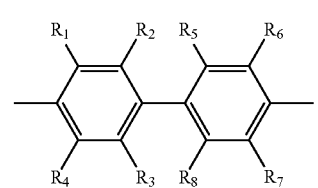

Formula 3b

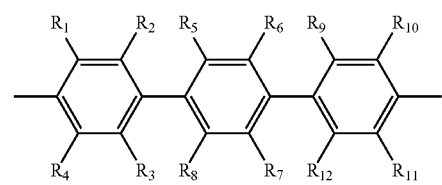

Formula 3c

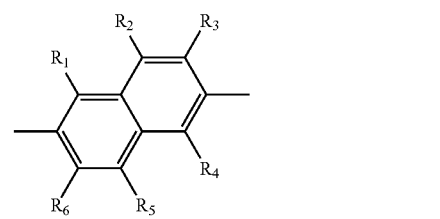

Formula 3d

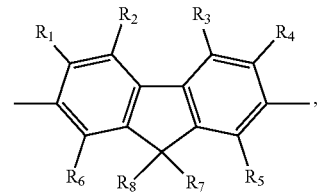

Formula 3e wherein, in Formulae 3a to 3e and 4a to 4r, $R_1$, $R_2$, $R_3$, $R_4$, $R_5$, $R_6$, $R_7$, $R_8$, $R_9$, $R_{10}$, $R_{11}$, and $R_{12}$ are each independently hydrogen, a halogen, a hydroxyl group, or a substituted or unsubstituted C1-C10 alkyl group, M3 and M6 are each independently a heteroarylene group represented by Formulae 4a to 4r,

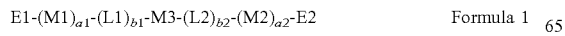

Formula 4a

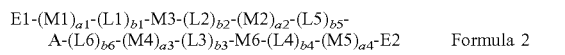

Formula 4b

-continued

Formula 4c
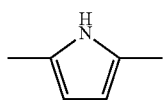

Formula 4d
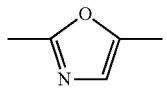

Formula 4e
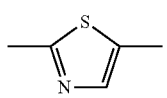

Formula 4f
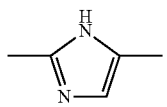

Formula 4g
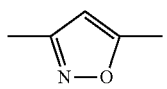

Formula 4h
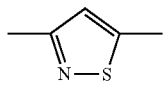

Formula 4i
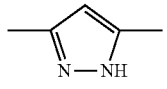

Formula 4j
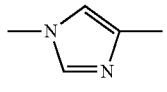

Formula 4k
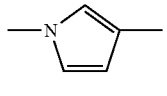

Formula 4l
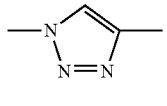

Formula 4m
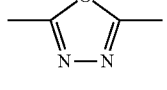

Formula 4n
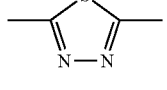

Formula 4o
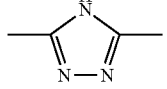

Formula 4p
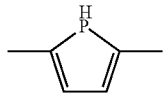

Formula 4q
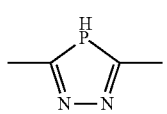

Formula 4r
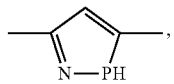

L1, L2, L3, L4, L5, and L6 are each independently —O—, —S—, —C(=O)—, —S(=O)—, —C(=O)O—, —O—C(=O)O—, —(CH$_2$)$_2$—C(=O)—, —CH=CH—C(=O)—, —CH=N—, —NH—C(=O)O—, —C(=O)—NH—, or —OC(=O)—NH—S(=O)O—, A is a substituted or unsubstituted C4-C12 alkylene group, a substituted or unsubstituted C4-C12 alkenylene group, a substituted or unsubstituted C4-C12 alkynylene group, or a substituted or unsubstituted C4-C12 alkadienylene group;

E1 and E2 are each independently an epoxy-containing group, a1, a2, a3, and a4 are each independently an integer from 0 to 2, where the sum of a1 and a2 is 1 to 4, and the sum of a3 and a4 is 1 to 4, and b1, b2, b3, and b4 are each independently 0 or 1, and b5 and b6 are each independently 1 or 2.

According to an aspect of an embodiment, an epoxy resin composition includes:

the epoxy compound described above; and a curing agent.

According to an aspect of an embodiment, a semiconductor device includes:

a substrate;

a semiconductor; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion including the cured product of the epoxy resin composition, a substrate portion including the cured product of the epoxy resin composition, a reinforcement portion including the cured product of the epoxy resin composition, or an attachment portion including the cured product of the epoxy resin composition.

According to an aspect of an embodiment, an electronic device includes:

a substrate;

an electronic component; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion including the cured product of the epoxy resin composition, a substrate portion including the cured product of the epoxy resin composition, a reinforcement portion including the cured product of the epoxy resin composition, or an attachment portion including the cured product of the epoxy resin composition.

According to an aspect of an embodiment, an article includes:

a substrate; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion including the cured product of the epoxy resin composition, a substrate portion including the cured product of the epoxy resin composition, a reinforcement portion including the cured product of the epoxy resin composition, or an attachment portion including the cured product of the epoxy resin composition.

According to an aspect of an embodiment, a method of preparing an article includes:

providing the epoxy resin composition described above on a substrate; and curing of the epoxy resin composition.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
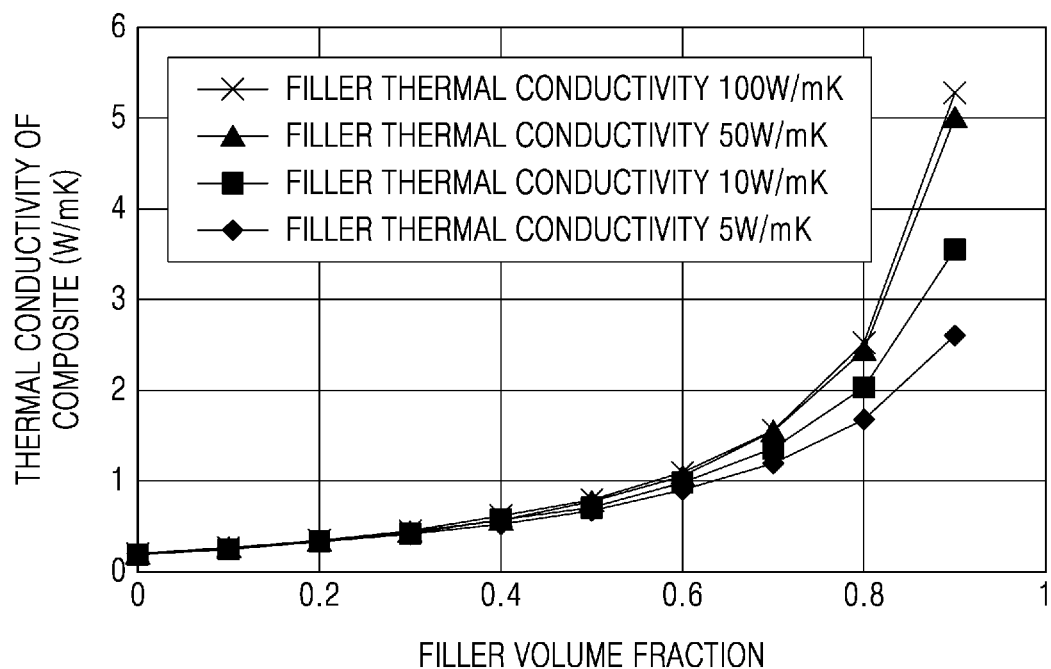
FIG. 1 is a graph that illustrates changes in thermal conductivity of a compound (also referred to as a composite) according to thermal conductivity of a filler.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list, for example, "at least one of a, b, or c" indicates only a, only b, only c, both a and b, both a and c, both b and c, all of a, b, and c, or variations thereof.

Various example embodiments will now be described more fully with reference to the accompanying drawings. This inventive concept may, however, be embodied in many different forms and should not be construed as limited to the exemplary embodiments set forth herein. Rather, these embodiments are provided so that this disclosure will be thorough and complete, and will fully convey the scope of the inventive concept to one of ordinary skill in the art. Like reference numerals in the drawings denote like elements.

It will be understood that when a component is referred to as being "on" another component, the component can be directly on the other component or intervening components may be present therebetween. In contrast, when a component is referred to as being "directly on" another component, an intervening component is not present therebetween.

While such terms as "first," "second," "third", etc., may be used to describe various elements, components, regions, layers, and/or sections, such elements, components, regions, layers, and/or sections must not be limited to the above terms. The above terms are used only to distinguish one element, component, region, layer, or section from another element, component, region, layer, or section. Therefore, a first element, component, region, layer, or section described hereinafter may be referred to as a second element, component, region, layer, or section without departing from the teachings of the present specification.

The terms used in the present specification are merely used to describe particular embodiments, and are not intended to limit the inventive concept. An expression used in the singular encompasses the expression of the plural including "at least one", unless it has a clearly different meaning in the context. The term "at least one" should not be understood as limiting to the singular. As used herein, the term "or" means "and/or," the term "and/or" includes any and all combinations of one or more of the associated list items. It will be further understood that the terms "includes," "have," "comprises," "including," "having," and/or "comprising," when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath", "below", "lower", "above", and "upper", may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations), and the spatially relative descriptors used herein may be interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments are described herein with reference to cross-sectional illustrations that are schematic illustrations of idealized example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, a region illustrated or described as flat may, typically, have rough and/or nonlinear features. Moreover, angles illustrated as sharp may be rounded. Thus, the regions illustrated in the figures are schematic in nature and their shapes are not intended to illustrate the actual shape of a region and are not intended to limit the scope of the present description.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±20%, 10%, 5% of the stated value.

While particular embodiments are described, alternatives, modifications, variations, improvements, and substantial equivalents that are or may be presently unforeseen or unexpected may arise to applicants or those skilled in the art. Accordingly, the appended claims as filed and as they may be amended are intended to embrace all such alternatives, modification, variations, improvements, and substantial equivalents.

Hereinafter, according to an embodiment, an epoxy compound, a composition prepared from the epoxy compound, a semiconductor device prepared from the epoxy compound, an electronic device prepared from the epoxy compound, an article prepared from the epoxy compound, and a method of preparing the article will be described in detail.

Epoxy Compound

According to an embodiment, an epoxy compound including a 5-membered aromatic heterocyclic ring is represented by Formula 1 or Formula 2:

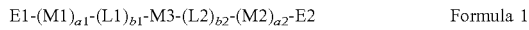

Formula 1

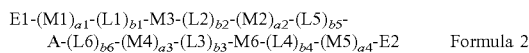

Formula 2

In Formulae 1 and 2,

M1, M2, M4, and M5 are each independently an arylene group represented by one of Formulae 3a to 3e, M3 and M6 are each independently a heteroarylene group represented by one of Formulae 4a to 4r, L1, L2, L3, L4, L5, and L6 are each independently —O—, —S—, —C(=O)—, —S(=O)—, —C(=O)O—, —O—C(=O)O—, —(CH$_2$)$_2$—C(=O)—, —CH=CH—C(=O)—, —CH=N—, —NH—C(=O)O—, —C(=O)—NH—, or —OC(=O)—NH—S(=O)O—, A is a substituted or unsubstituted C4-C12 alkylene group, a substituted or unsubstituted C4-C12 alkenylene group, a substituted or unsubstituted C4-C12 alkynylene group, or a substituted or unsubstituted C4-C12 alkadienylene group;

E1 and E2 are each independently an epoxy-containing group, E1 and E2 are each independently the same or different;

a1, a2, a3, and a4 are each independently an integer from 0 to 2, where the sum of a1 and a2 is 1 to 4, and the sum of a3 and a4 is 1 to 4, and b1, b2, b3, and b4 are each independently 0 or 1, and b5 and b6 are each independently 1 or 2.

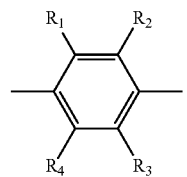

Formula 3a

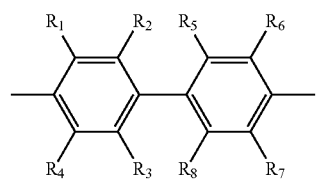

Formula 3b

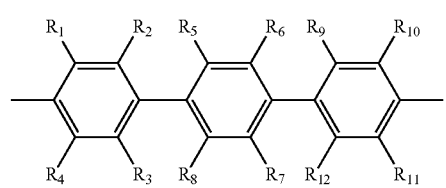

Formula 3c

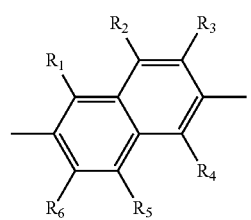

Formula 3d

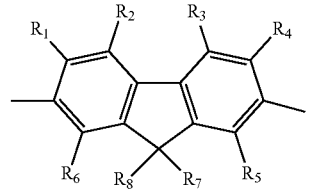

Formula 3e

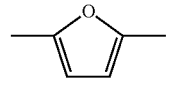

Formula 4a

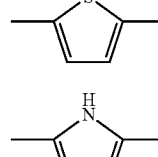

Formula 4b

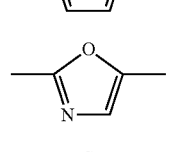

Formula 4c

Formula 4d

Formula 4e

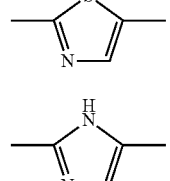

Formula 4f

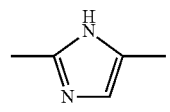

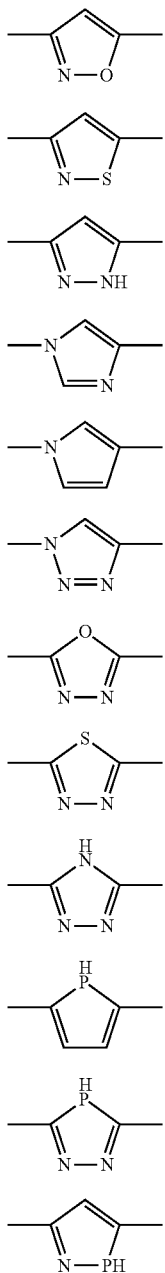

Formula 4g
Formula 4h
Formula 4i
Formula 4j
Formula 4k
Formula 4l
Formula 4m
Formula 4n
Formula 4o
Formula 4p
Formula 4q
Formula 4r In Formulae 3a to 3e, $R_1$, $R_2$, $R_3$, $R_4$, $R_5$, $R_6$, $R_7$, $R_8$, $R_9$, $R_{10}$, $R_{11}$, and $R_{12}$ are each independently a hydrogen, a halogen, a hydroxyl group, or a substituted or unsubstituted C1-C10 alkyl group.

In Formula 2, A may be, for example, a C4-C12 alkylene group which is unsubstituted or substituted with a halogen, a C4-C12 alkenylene group which is unsubstituted or substituted with a halogen, a C4-C12 alkynylene group which is unsubstituted or substituted with a halogen, or a C4-C12 alkadienylene group which is unsubstituted or substituted with a halogen. The epoxy compound including a 5-membered aromatic heterocyclic ring represented by Formula 1 or 2 does not contain a structure of —O—O—, —O—S—, or —S—S—.

A resin is generally a thermal insulator, and a thermal conductivity of the resin is in a range of about 0.1 Watts per meter Kelvin (W/mK) to about 0.2 W/mK. Heat is transferred in a resin, which is a thermal insulator, by vibration transmission of phonons, but a thermal conductivity of the resin may become low because of a scattering of phonons. A thermal conductivity of a resin that is used as a semiconductor package material may be, for example, in a range of about 0.1 W/mK to about 0.2 W/mK. Even when a filler having a high thermal conductivity is added to the resin, an increase in a thermal conductivity of the compound is not significant. For example, FIG. 1 is a graph that illustrates changes in a thermal conductivity of a compound according to a thermal conductivity of a filler. FIG. 1 shows a change in a thermal conductivity of a compound including a filler and a resin as an amount of the filler increased from about 1 vol % to about 90 vol % in the resin having a thermal conductivity of about 0.2 W/mK, where the results are calculated based on the Maxwell Model. As shown in FIG. 1, at an amount of the filler of about 90 vol %, a thermal conductivity of the compound converges to about 5 W/mK even when a thermal conductivity of the filler increases to about 50 W/mK or higher. That is, in the compound including the filler and the resin, a thermal conductivity of the compound converges to about 5 W/mK and does not increase any higher even when a thermal conductivity of the filler increases to about 100 W/mK.

Figure 2:
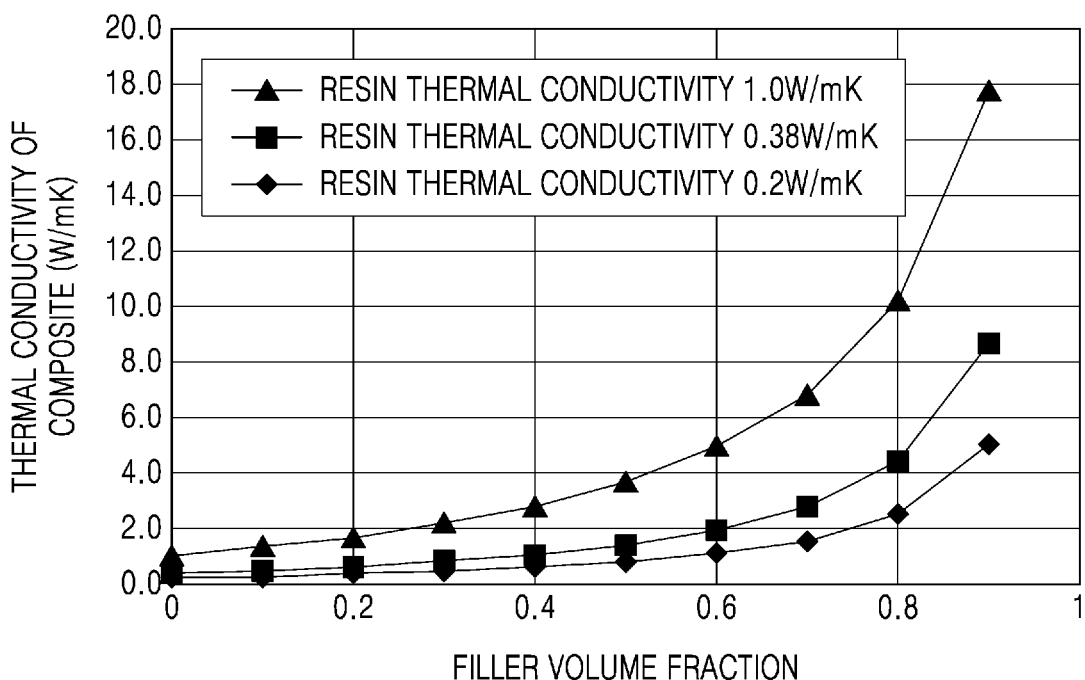
FIG. 2 is a graph that illustrates changes in thermal conductivity of a compound according to thermal conductivity of a resin.

In an embodiment, the epoxy compound including a 5-membered aromatic heterocyclic ring represented by Formula 1 has a mesogenic unit that contains a plurality of aromatic rings in the main chain. While not wishing to be bound by theory, it is understood that when the plurality of aromatic rings in the mesogenic unit form π-π stacking and intermolecular hydrogen bonding, chain stiffness of the main chain of the epoxy compound may increase, and molecular ordering of the epoxy compound may increase. As a result, a phonon transfer pathway may be provided in the resin, which is an epoxy compound and/or its cured product. Thus, a thermal conductivity of the epoxy compound and/or its cured product may increase. In an embodiment, the mesogenic unit in the epoxy compound including a 5-membered aromatic heterocyclic ring represented by Formula 1 may include a heteroaromatic ring. A hetero atom of the heteroaromatic ring may form additional bonds such as hydrogen bonds with adjacent epoxy compounds and thus may provide an additional phonon transfer pathway in the resin. In an embodiment, a thermal conductivity of the resin, which is an epoxy compound and/or its cured product, may further increase. In an embodiment, the epoxy compound including an aromatic heterocyclic ring represented by Formula 2 may further include a spacer having flexibility between the mesogenic units. When the spacer is further introduced in the epoxy compound, for example, a liquid crystal like structure such as a smectic phase may be formed. Molecular ordering of an epoxy compound and/or and a resin prepared therefrom may increase by including a high ordered domain such as the liquid crystal like structure. As a result, phonon scattering in the resin, which is an epoxy compound and/or its cured product, may be suppressed. Thus, a thermal conductivity of the resin, which is an epoxy compound and/or its cured product, may further increase. In an embodiment, when the resin, which is a cured product prepared from an epoxy compound represented by Formula 1 and/or 2, has a high thermal conductivity, a thermal conductivity of the compound including the resin may significantly increase. For example, FIG. 2 is a graph that illustrates changes in a thermal conductivity of a compound according to a thermal conductivity of a resin. FIG. 2 shows changes in a thermal conductivity value of a compound including a filler and a resin according to an amount of the filler while a thermal conductivity of an $Al_2O_3$ filler is fixed to a thermal conductivity of about 50 W/mK and a thermal conductivity of the resin is increased from about 0.2 W/mK to about 1.0 W/mK, where the results are calculated based on the Maxwell Model. As shown in FIG. 2, at an amount of the filler of about 90 vol %, a thermal conductivity of the compound increased up to about 18 W/mK, when a thermal conductivity of the resin is increased from about 0.2 W/mK to about 1.0 W/mK.

The epoxy compound represented by Formula 1 may be, for example, an epoxy compound represented by one of Formulae 5a to 5f:

| Formula 5a | Formula 5b | Formula 5c |
|---|---|---|
| E1-M1-L7-M3-L8-M2-E2 | E1-M1-L7-M3-E2 | E1-M3-L8-M2-E2 |
| Formula 5d | Formula 5e | Formula 5f |
| E1-M1-M3-M2-E2 | E1-M1-M3-E2 | E1-M3-M2-E2 |

In Formulae 5a to 5f, M1 and M2 may be each independently an arylene group represented by one of Formulae 3a to 3e, M3 may be a heteroarylene group represented by one of Formulae 4a to 4r, L7 and L8 may be each independently —O—, —C(=O)—, —C(=O)O—, or —O—C(=O)O—, and E1 and E2 may be each independently an epoxy-containing group, E1 and E2 may be each independently the same or different.

The epoxy compound represented by Formula 2 may be, for example, an epoxy compound represented by one of Formulae 6a to 6f:

E1-M1-L9-M3-L10-M2-L13-A1-L14-M4-L11-M6-L12-M5-E2  Formula 6a

E1-M1-L9-M3-L13-A1-L14-M4-L11-M6-E2  Formula 6b

E1-M3-L10-M2-L13-A1-L14-M6-L12-M5-E2  Formula 6c

E1-M1-M3-M2-L13-A1-L14-M4-M6-M5-E2  Formula 6d

E1-M1-M3-L13-A1-L14-M4-M6-E2  Formula 6e

E1-M3-M2-L13-A1-L14-M6-M5-E2  Formula 6f

In Formulae 6a to 6f, M1, M2, M4 and M5 may be each independently at least one arylene group represented by one of Formulae 3a to 3e, M3 and M6 may be each independently a heteroarylene group represented by one of Formulae 4a to 4r, L9, L10, L11, and L12 may be each independently —O—, —S—, —C(=O)—, —S(=O)—, —C(=O)O—, or —O—C(=O)O—, L13 and L14 may be each independently —O— or —S—, A1 may be a C4-C12 alkylene group partially or fully substituted with halogen, an unsubstituted C4-C12 alkylene group, a C4-C12 alkadienylene group partially or fully substituted with halogen, or an unsubstituted C4-C12 alkadienylene group, and E1 and E2 may be each independently an epoxy-containing group, E1 and E2 may be each independently the same or different.

In the epoxy compound including a 5-membered aromatic heterocyclic ring represented by one of Formulae 6a to 6f, A1 may be, for example, a butylene group, a pentylene group, a hexylene group, a heptylene group, an octylene group, a nonylene group, a decylene group, an undecylene group, a dodecylene group, a butadienylene group, a pentadienylene group, a hexadienylene group, a heptadienylene group, an octadienylene group, a nonadienylene group, a decadienylene group, an undecadienylene group, or a dodecadienylene group. For example, A1 may be a butylene group, a pentylene group, a hexylene group, a heptylene group, an octylene group, a nonylene group, a decylene group, an undecylene group, or a dodecylene group. For example, A1 may be a butylene group, a hexylene group, an octylene group, or a decylene group.

In the epoxy compound including a 5-membered aromatic heterocyclic ring represented by Formula 1 or Formula 2, E1 and E2 may be each independently the same or different, for example, E1 and E2 may be each independently an epoxy-containing group represented by one of Formulae 7a to 7d:

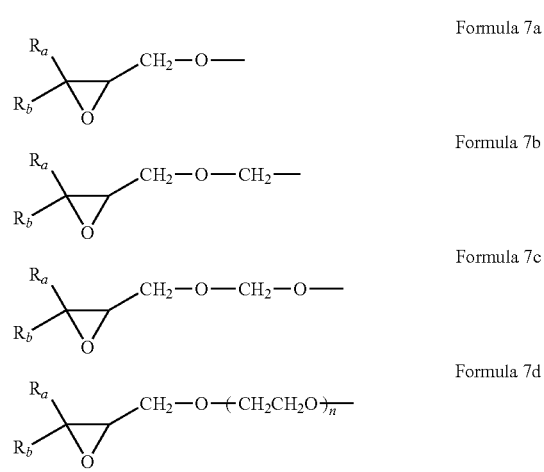

In Formulae 7a to 7d, $R_a$ and $R_b$ may be each independently a hydrogen, a halogen, a hydroxyl group, or a substituted or unsubstituted C1-C10 alkyl group, and n is an integer from 1 to 10.

In the epoxy compound including a 5-membered aromatic heterocyclic ring represented by Formula 1 or Formula 2, M1, M2, M4, and M5 may be each independently the same or different, for example, M1, M2, M4, and M5 may be each independently an arylene group represented by one of Formulae 8a to 8e, and E1 and E2 may be each independently the same or different, for example, E1 and E2 may be each independently an epoxy-containing group represented by one of Formulae 9a to 9d:

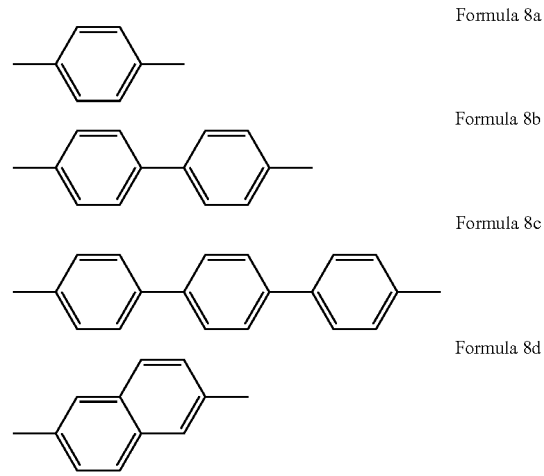

-continued

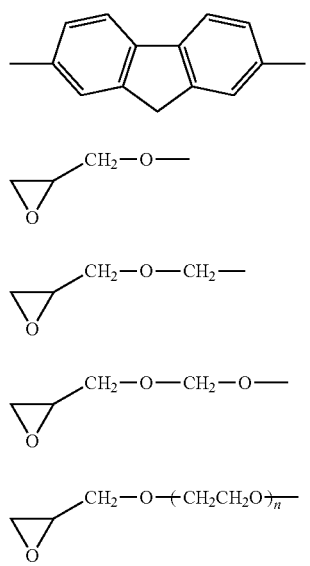

In Formulae 9a to 9d, n is an integer from 1 to 10.

The epoxy compound including a 5-membered aromatic heterocyclic ring represented by Formula 1 may be an epoxy compound represented by one of Formulae 10a to 10o and 11a to 11r:

Formula 10a
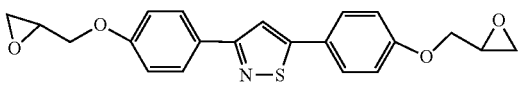

Formula 10b
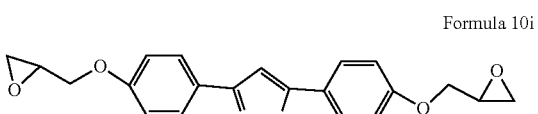

Formula 10c
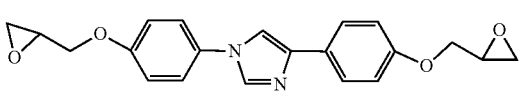

Formula 10d
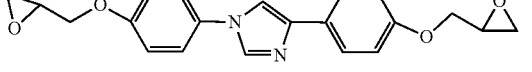

Formula 10e
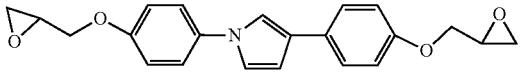

Formula 10f
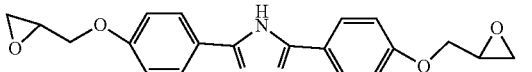

Formula 10g
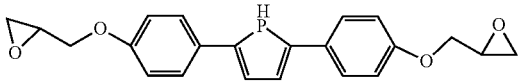

Formula 10h
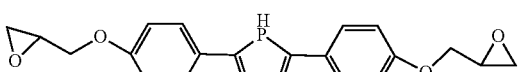

Formula 10i

Formula 10j
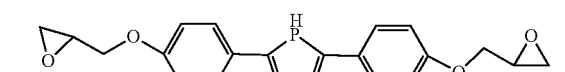

Formula 10k
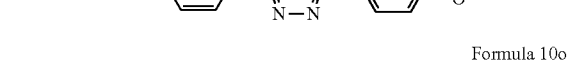

Formula 10l
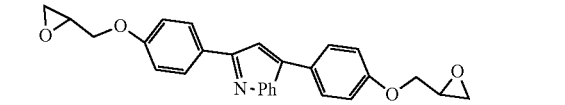

Formula 10m
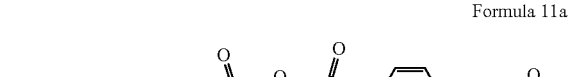

Formula 10n

Formula 10o

Formula 11a
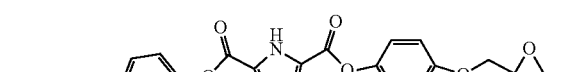

Formula 11b

Formula 11c

Formula 11d
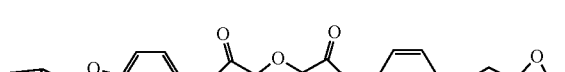

Formula 11e
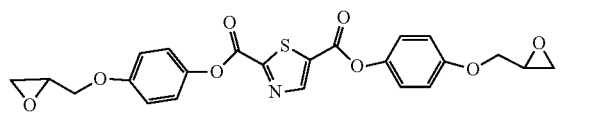
Formula 11f
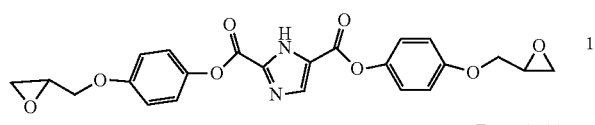
Formula 11g
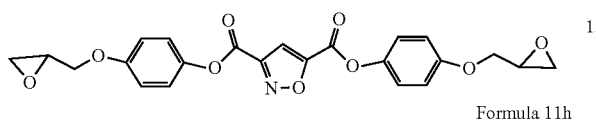
Formula 11h
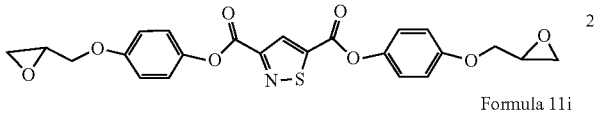
Formula 11i
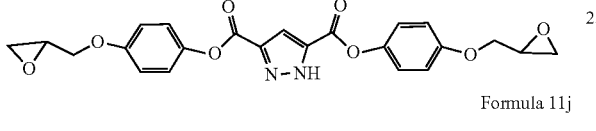
Formula 11j
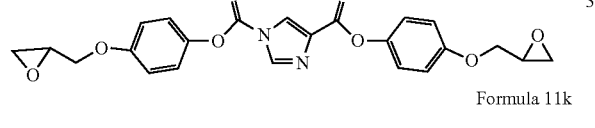
Formula 11k
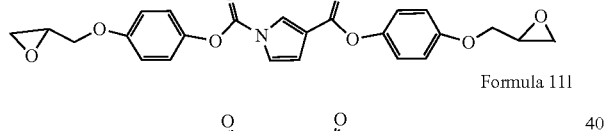
Formula 11l
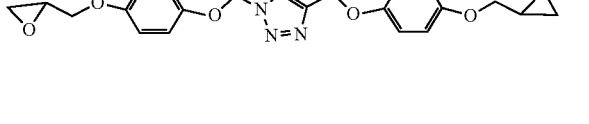
Formula 11m
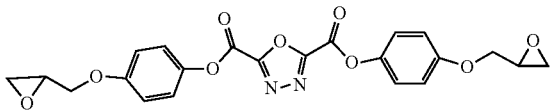
Formula 11n
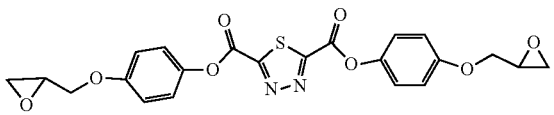
Formula 11o
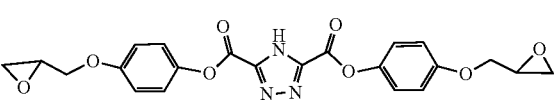
Formula 11p
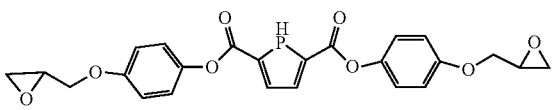
Formula 11q
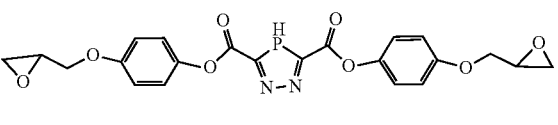
Formula 11r
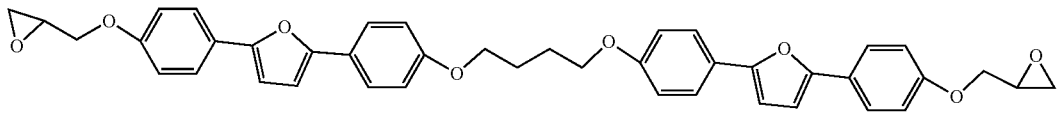
The epoxy compound including a 5-membered aromatic heterocyclic ring represented by Formula 2 may be an epoxy compound represented by one of Formulae 12a to 12r and 13a to 13r:
Formula 12a
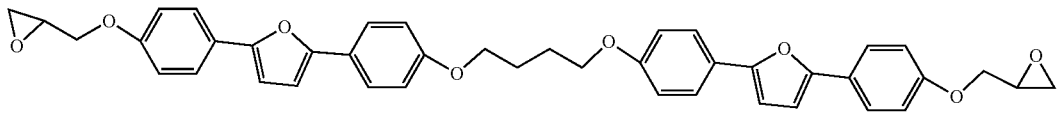
Formula 12b
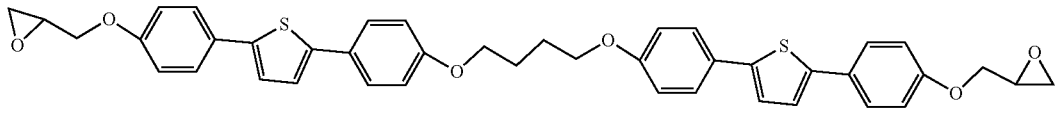
Formula 12c
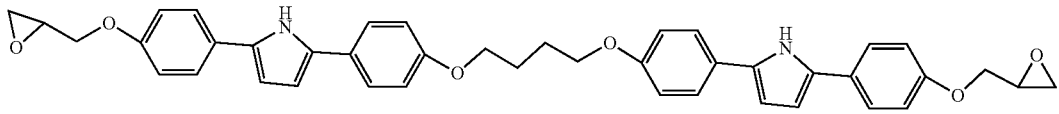

-continued
Formula 12d
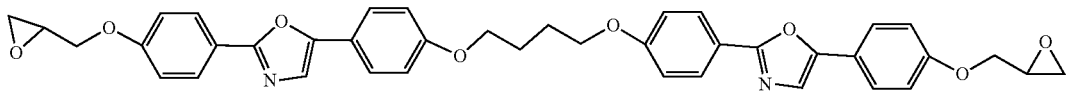
Formula 12e
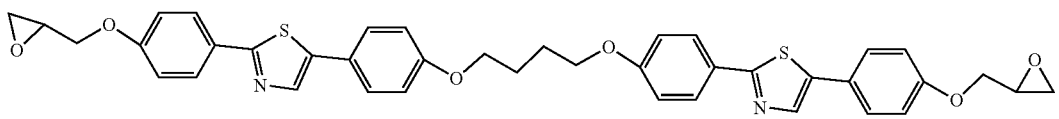
Formula 12f
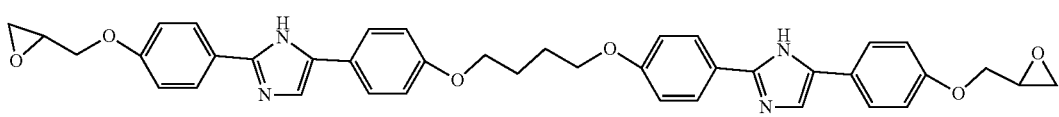
Formula 12g
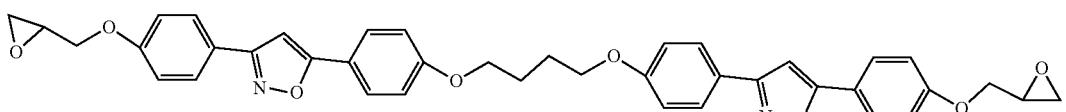
Formula 12h
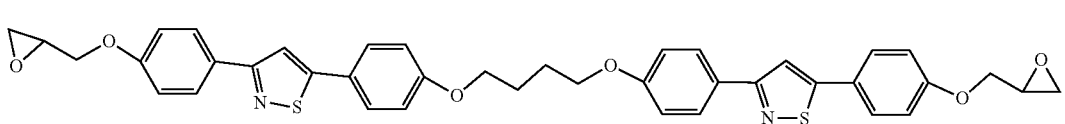
Formula 12i
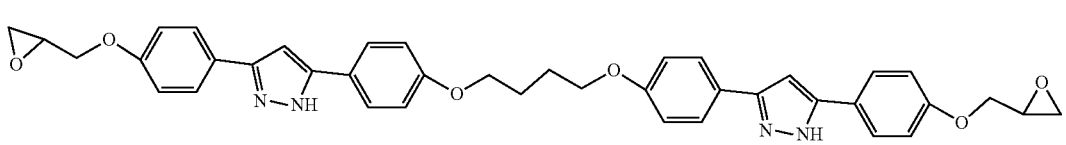
Formula 12j
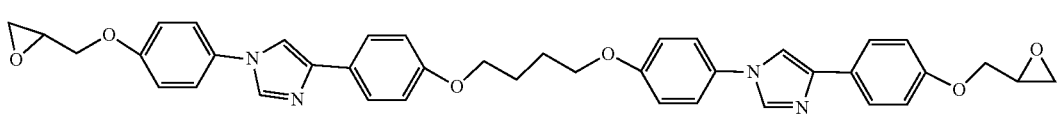
Formula 12k
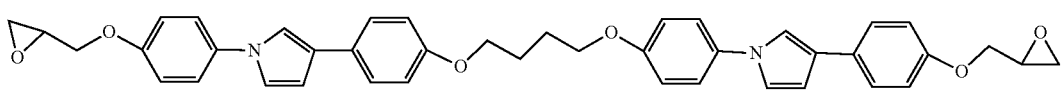
Formula 12l
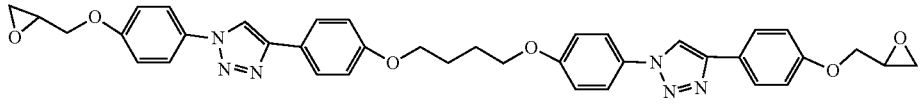
Formula 12m
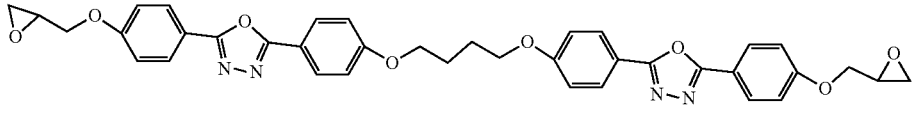
Formula 12n
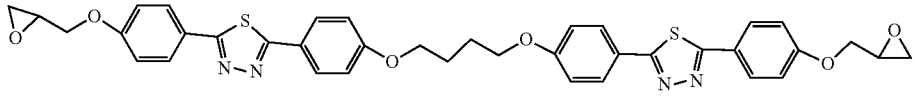
Formula 12o
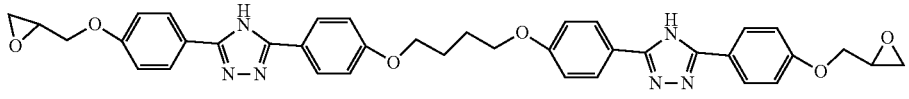

-continued
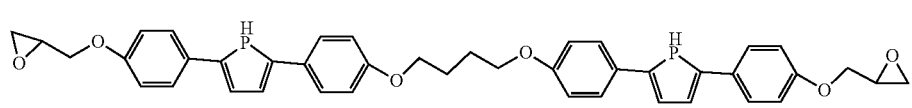
Formula 12p
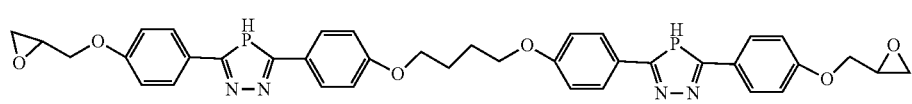
Formula 12q
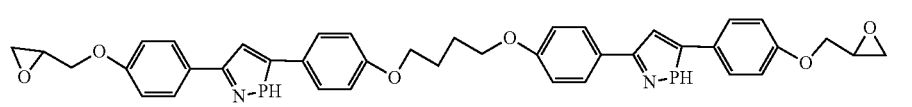
Formula 12r
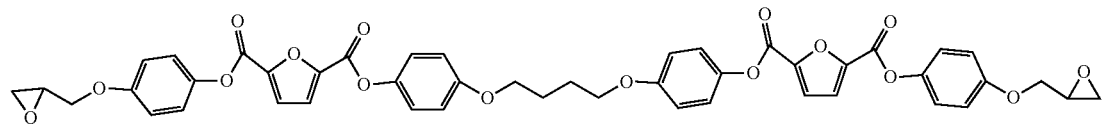
Formula 13a
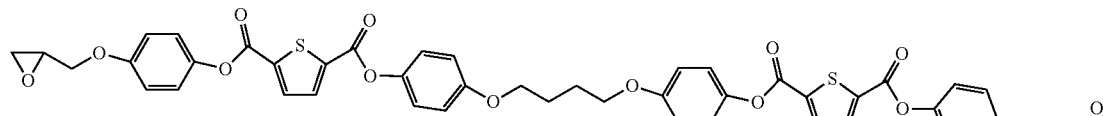
Formula 13b
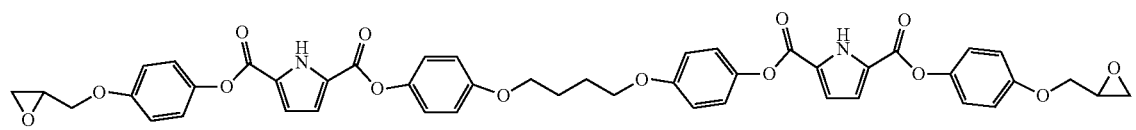
Formula 13c
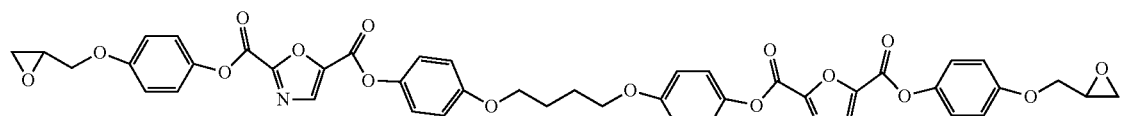
Formula 13d
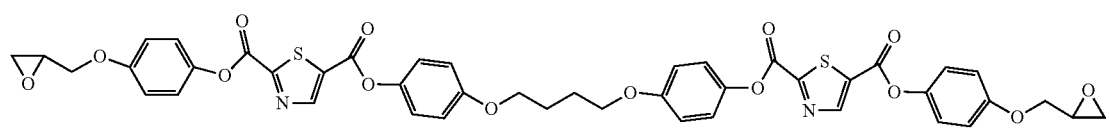
Formula 13e
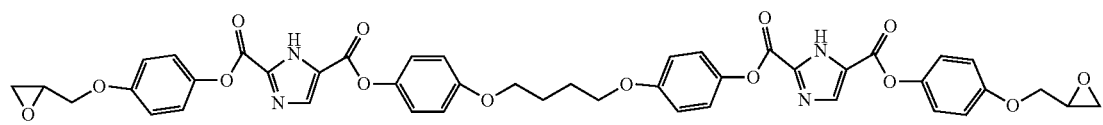
Formula 13f
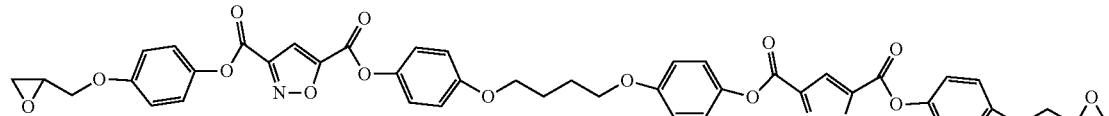
Formula 13g
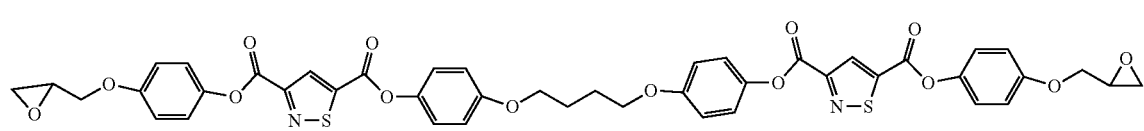
Formula 13h -continued Formula 13i
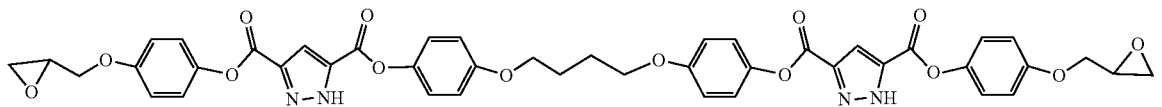

Formula 13j
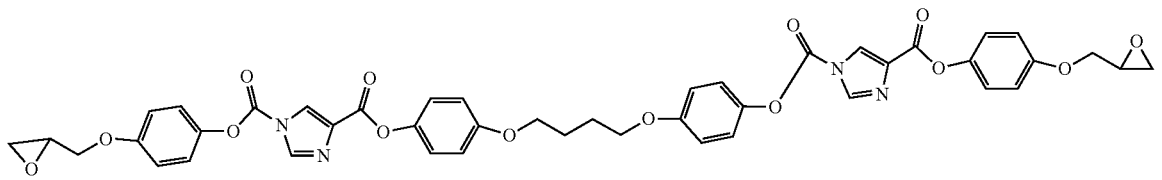

Formula 13k
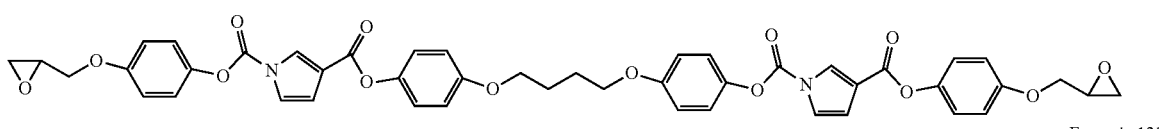

Formula 13l
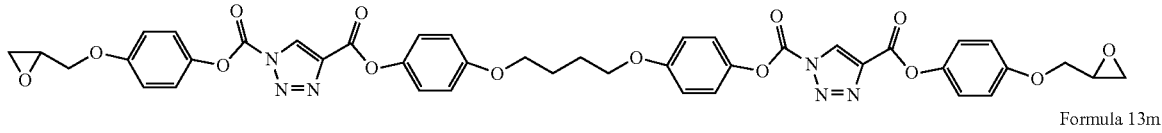

Formula 13m
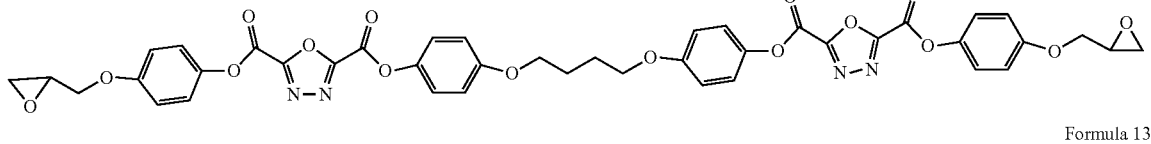

Formula 13n
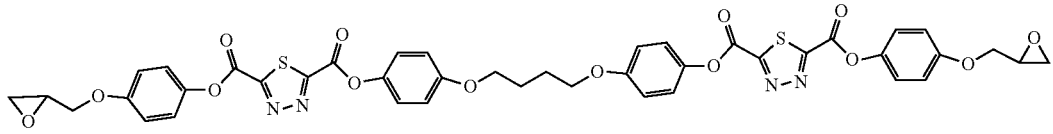

Formula 13o
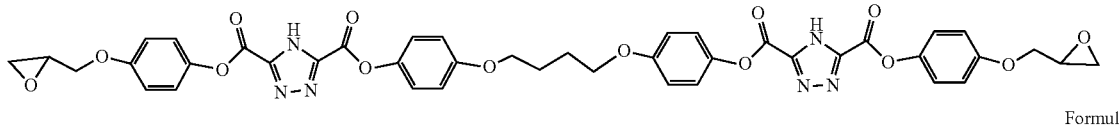

Formula 13p
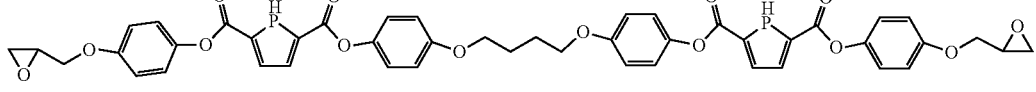

Formula 13q
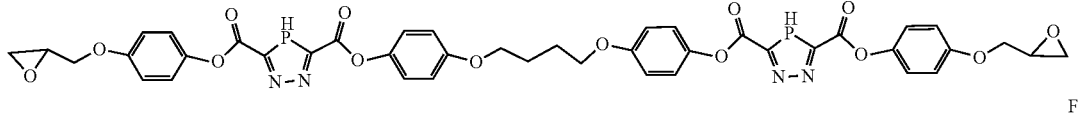

Formula 13r
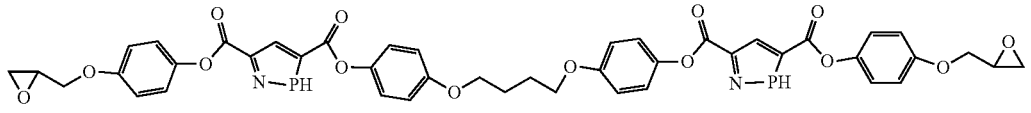

A melting point of the epoxy compound represented by Formula 1 or Formula 2 may be, for example, about 200° C. or lower, about 195° C. or lower, about 190° C. or lower, or about 185° C. or lower. A melting point of the epoxy compound represented by Formula 1 or Formula 2 may be, for example, about 30° C. to about 200° C., about 50° C. to about 200° C., about 80° C. to about 195° C., about 100° C. to about 190° C., or about 120° C. to about 185° C. While not wishing to be bound by theory, it is understood that when the epoxy compound represented by Formula 1 and Formula 2 has a melting point within these ranges, a curing temperature of the epoxy resin composition may decrease, and thus, damages such as thermal deformation of electronic components due to a too high temperature may be prevented during curing of the epoxy resin composition.

Since the epoxy compound of Formula 2 further include a spacer (A), a melting point of the epoxy compound of Formula 2 may be lower than that of the epoxy compound of Formula 1. For example, a melting point of the epoxy compound of Formula 2 may be about 95% or lower, about 90% or lower, or about 80% or lower than that of the epoxy compound of Formula 1. For example, the melting point of the epoxy compound of Formula 2 may be about 95% to about 1%, about 80% to about 1%, about 60% to about 5%, about 50% to about 5%, about 40% to about 10%, or about 30% to about 10% lower than that of the epoxy compound of Formula 1. For example, when a melting point of the epoxy compound of Formula 1 is about 180° C., a melting point of the epoxy compound of Formula 2 may be about 171° C. or lower. Epoxy resin composition According to an embodiment, an epoxy resin composition includes an epoxy compound represented by one of Formula 1, Formula 2, Formulae 5a to 5f, Formulae 6a to 6f, Formulae 10a to 10o, Formulae 11a to 11r, Formulae 12a to 12r, and Formulae 13a to 13r described above; and a curing agent. When the epoxy resin composition includes the epoxy compound, a cured product of the epoxy resin composition may provide improved thermal conductivity. The epoxy resin composition may be molded into various forms.

The curing agent in the epoxy resin composition may be, for example, an amine-based curing agent, an acid anhydride-based curing agent, a polyamine curing agent, a polysulfide curing agent, a phenolic novolak type curing agent, a bisphenol A type curing agent, and a dicyandiamide curing agent, but embodiments are not limited thereto. The curing agent may be, for example, a polyfunctional phenol-based curing agent. The polyfunctional phenol-based curing agent may be, for example, a compound having at least three phenolic hydroxyl groups, and the compound may have the following structure.

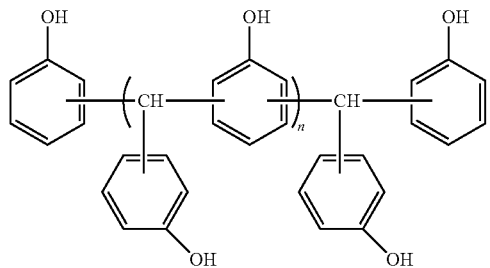

Where, n is an integer of 1 to 10000.

A number average molecular weight of the polyfunctional phenol-based curing agent may be, for example, in a range of about 300 dalton to about 30000 dalton, about 400 dalton to about 30000 dalton, about 600 dalton to about 10000 dalton, or about 800 dalton to about 10000 dalton.

An amount of the curing agent may be in a range of about 0.1 parts to about 10 parts by weight, about 0.1 parts to about 5 parts, or about 0.1 parts to about 1 part by weight based on 100 parts by weight of the epoxy resin composition, but embodiments are not limited thereto. When an amount of the curing agent is within these ranges, deterioration of insulating characteristics of the compound may be prevented by minimizing an amount of an unreacted curing agent while increasing a curing rate of the epoxy resin composition.

The epoxy resin composition may further include, for example, a filler, and the filler may be an inorganic filler, an organic filler, or a combination thereof.

The inorganic filler may be, for example, at least one of silicon oxide, calcium carbonate, magnesium carbonate, magnesia, clay, alumina ($Al_2O_3$), titania ($TiO_2$), talc, calcium silicate, antimony oxide, glass fiber, or eucryptite ceramic, but embodiments are not limited thereto. The eucryptite ceramic may be a crystallized glass composed of $Li_2O$, $Al_2O_3$, and $SiO_2$ components. The organic filler may include, for example, at least one of polyethylene imine, or polyethylene glycol, but embodiments are not limited thereto. The filler may be an inorganic filler in terms of having high thermal conductivity, strengthening the rigidity of the compound, and reducing the linear expansion coefficient.

An amount of the filler may be, for example, in a range of about 20 weight % (wt %) to about 99 wt %, about 30 wt % to about 99 wt %, about 40 wt % to about 99 wt %, about 50 wt % to about 99 wt %, about 60 wt % to about 99 wt %, about 70 wt % to about 99 wt %, about 80 wt % to about 99 wt %, about 90 wt % to about 99 wt %, or about 95 wt % to about 99 wt % based on the total weight of the epoxy resin composition. When an amount of the filler in the epoxy resin composition is within these ranges, properties such as moldability, low-stress property, high-temperature strength, and thermal expansion coefficient may be effectively controlled.

The epoxy resin composition may further include at least one additive from a curing accelerator, a reaction modifier, a releasing agent, a coupling agent, a stress reliever, or an auxiliary flame retardant. The additives may be each independently included in the epoxy resin composition at an amount, for example, in a range of about 0.1 parts to about 10 parts by weight, about 0.1 parts to about 5 parts by weight, about 0.1 parts to about 3 parts by weight, or about 0.1 parts to about 1 parts by weight based on 100 parts by weight of the epoxy resin composition.

The epoxy resin composition may further include any conventional or suitable epoxy resins in addition to the epoxy compound according to an embodiment. When the epoxy resin composition includes any conventional or any suitable epoxy resins, thermal expansion coefficient, warpage, and processing characteristics of the compound may further be improved, and peeling strength of the epoxy resin composition may also be improved. Examples of the conventional or suitable epoxy resins may include a biphenyl epoxy resin, a novolac epoxy resin, a dicyclopentadienyl epoxy resin, a bisphenol epoxy resin, a terpene epoxy resin, an aralkyl epoxy resin, a multi-functional epoxy resin, a naphthalene epoxy resin, and a halogenated epoxy resin. These epoxy resins may be used alone or in admixture of two or more. An amount of the conventional or suitable epoxy resin may be, for example, in a range of about 1 part to about 15 parts by weight, about 1 part to about 10 parts by weight, about 1 part to about 5 parts by weight based on 100 parts by weight of the epoxy resin composition, but embodiments are not limited thereto. When the epoxy resin composition further includes the conventional epoxy resin at an amount within these ranges, for example, adhesion between the epoxy resin composition and a substrate on a semiconductor package, thermal expansion coefficient, and processing properties of the compound may further be improved.

The epoxy resin composition may be used for various purposes. For example, the epoxy resin composition may be used as an encapsulating resin composition or a fixing resin composition. The encapsulating resin composition (a resin composition for encapsulating an electronic compartment) may be, for example, a resin composition for encapsulating a semiconductor capable of encapsulating electronic compartments such as a semiconductor chip and used in a semiconductor package, a resin composition for encapsulating electronic control units for vehicles, in which a substrate having electronic compartments mounted thereon is encapsulated, or a resin composition for encapsulating a sensor, a sensor module, a camera, a camera module, a module with an indicator, a module with a battery, or a module with a coin battery. The fixing resin composition may be, for example, a fixing resin composition of a motor compartment. The fixing resin composition of a motor compartment may be, for example, a resin composition for fixing a rotor core magnet or for fixing a stator. The epoxy resin composition may be used for purposes other than those described above.

A method of preparing an epoxy resin composition is not particularly limited. The method of preparing an epoxy resin composition may include selecting ingredients such as an epoxy compound and a curing agent; and mixing the ingredients. For example, an epoxy compound appropriate for an epoxy resin composition may be represented by Formula 1 and/or Formula 2. Subsequently, the epoxy compound may be mixed with other ingredients such as a curing agent or an additive to prepare a mixture as an epoxy resin composition.

In the mixing of the ingredients, the mixture may be obtained using any suitable method. Also, the mixture may be, for example, melt-kneaded at a temperature lower than the curing temperature of the epoxy resin composition to obtain a kneaded product. As the kneading method, for example, a kneading extruder such as a monoaxial kneading extruder or a biaxial kneading extruder may be used or a roll-type kneader such as a mixing roll may be used, but the biaxial kneading extruder may be preferably used. After cooling the kneaded product in the melted state, the kneaded product may be molded into a powdery, granular, tablet, or sheet shape. As a method of preparing a resin composition of a powdery shape, for example, a method of pulverizing a kneaded product using a pulverizing device may be used. The kneaded product may be molded into a sheet and then pulverized. A device used in the pulverization may be, for example, a hammer mill, a mortar grinder, or a roll crusher. A method of preparing a resin composition having a granular shape or a powdery shape may include, for example, processing method represented by a hot-cut technique, in which a dice having a small diameter is installed on a discharge port of a kneading device, and the molten kneaded product discharged from the dice is cut into a predetermined length by a cutter. After preparing the resin composition having a granular shape or a powdery shape using the processing method such as the hot-cut technique, degassing of the resin composition may be performed while the temperature of the resin composition is not much lowered.

Semiconductor Device

According to an embodiment, a semiconductor device includes a substrate; a semiconductor; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion formed of a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a substrate portion formed of a cured product of an epoxy resin composition including a curing agent and an epoxy compound including a 5-membered aromatic heterocyclic ring and represented by Formula 1, an epoxy compound having a 5-membered aromatic heterocyclic ring and represented by Formula 2, or a combination thereof, a reinforcement portion formed of a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, or an attachment portion formed of a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof. When the semiconductor device includes at least one of the cured product, sealing portion, substrate portion, reinforcement portion, or attachment portion, heat release characteristics of the semiconductor device may be improved, and as a result, thermal stability of the semiconductor device may be improved.

A thermal conductivity of the cured product of the epoxy resin composition in the semiconductor device may be, for example, about 0.4 W/mK or higher, about 0.45 W/mK or higher, about 0.5 W/mK or higher, about 0.55 W/mK or higher, or about 0.6 W/mK or higher. A thermal conductivity of the cured product of the epoxy resin composition in the semiconductor device may be, for example, in a range of about 0.4 W/mK to about 50 W/mK, about 0.45 W/mK to about 45 W/mK, about 0.5 W/mK to about 40 W/mK, about 0.55 W/mK to about 30 W/mK, about 0.55 W/mK to about 20 W/mK, about 0.55 W/mK to about 10 W/mK, or about 0.6 W/mK to about 10 W/mK. When a thermal conductivity of at least one of the cured product, sealing portion, substrate portion, reinforcement portion, or attachment portion in the semiconductor device is within these ranges, thermal stability of the semiconductor device may further be improved.

Because the epoxy compound of Formula 2 further includes a spacer (A), a thermal conductivity of the cured product of the epoxy resin composition including the epoxy compound of Formula 2 may be higher than that of a cured product of the epoxy resin composition including the epoxy compound of Formula 1. For example, a thermal conductivity of the cured product of the epoxy resin composition including the epoxy compound of Formula 2 may be, for example, about 110% to about 200%, about 120% to about 200%, about 130% to about 200%, about 150% to about 200%, or about 160% to about 200% of a thermal conductivity of the cured product of the epoxy resin composition including the epoxy compound of Formula 1. For example, when a thermal conductivity of the cured product of the epoxy resin composition including the epoxy compound of Formula 1 is about 0.50 W/mK, a thermal conductivity of the cured product of the epoxy resin composition including the epoxy compound of Formula 2 may be about 0.55 W/mK or higher.

Figure 3:
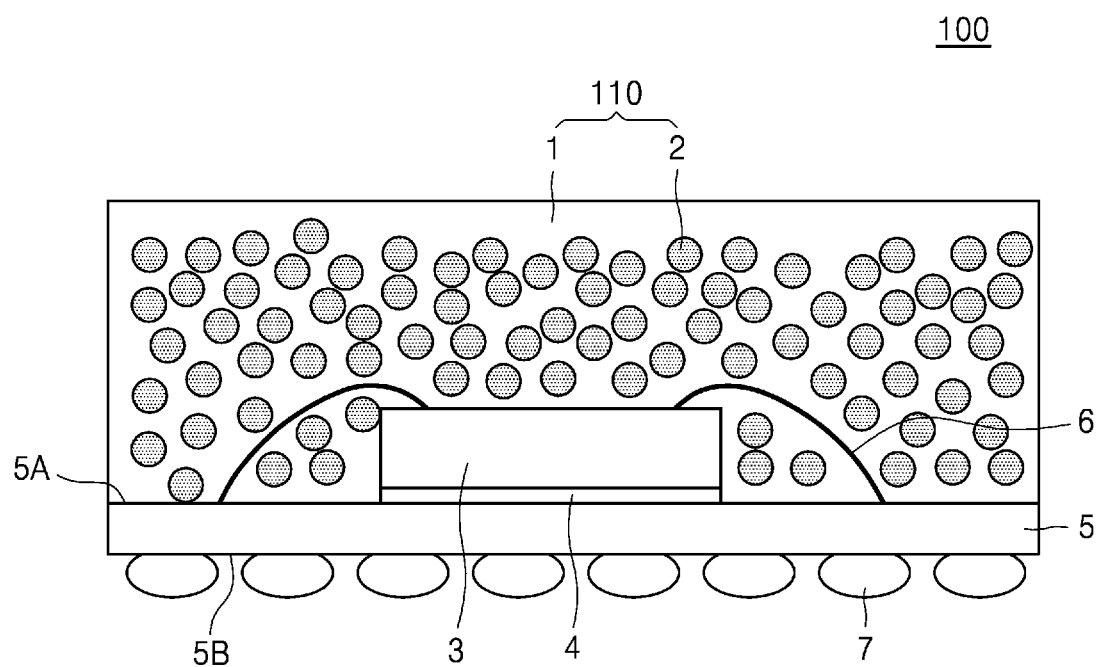
FIG. 3 is a schematic cross-sectional view of a semiconductor device according to an embodiment.

The semiconductor device may be, for example, a semiconductor package. Referring to FIG. 3, a semiconductor package 100 includes a substrate 5; a die attach film 4 placed on the substrate 5; a semiconductor chip 3 placed on the substrate 5 and attached to the substrate 5 through the die attach film 4; coupling portions 6 such as bonding wires that electrically connect the semiconductor chip 3 and the substrate 5; and a molding portion 110 that encapsulates the semiconductor chip 3 and the coupling portions 6 and for protecting the substrate 5 and an accommodation structure including the semiconductor chip 3 and the coupling portions 6 mounted on the substrate 5. The molding portion 110 is formed to completely encapsulate the semiconductor chip 3 and the coupling portions 6 on the substrate 5. The molding portion 110 may be prepared from the epoxy resin composition described herein. The molding portion 110 may include an epoxy resin 1 and fillers 2 dispersed in the epoxy resin 1. The molding portion 110 may have a form in which fillers dispersed in a resin matrix formed by curing an epoxy compound. A plurality of solder balls 7 that electrically connect the semiconductor chip 3 to an external circuit (not shown) are formed on a surface 5B of the substrate 5 opposite to an accommodation surface 5A on which the semiconductor chip 3 is mounted. In order to prepare a semiconductor package using an epoxy resin composition, for example, the semiconductor package 100 shown in FIG. 3, a process of forming the molding portion 110 that encapsulate the semiconductor chip 3 mounted on the substrate 5 may be performed using a low-pressure transfer molding process. In an embodiment, for example, an injection molding process or a casting process may be used instead of the low-pressure transfer molding process. The molding portion 110 formed using the epoxy resin composition may protect a region of the semiconductor chip 3 from moisture in the semiconductor package 100 and provide improved heat release characteristics. Thus, the reliability of the semiconductor package 100 may be improved even in a humid environment.

Electronic Device

According to an embodiment, an electronic device includes a substrate; an electronic component; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion including the cured product of the epoxy resin composition, a substrate portion including the cured product of the epoxy resin composition, a reinforcement portion including the cured product of the epoxy resin composition, or an attachment portion including the cured product of the epoxy resin composition. When the electronic device includes at least one of the cured product, sealing portion, substrate portion, reinforcement portion, or attachment portion, heat release characteristics of the electronic device may be improved, and as a result, thermal stability of the electronic device may be improved.

A thermal conductivity of the cured product of the epoxy resin composition in the electronic device may be, for example, about 0.4 W/mK or higher, about 0.45 W/mK or higher, about 0.5 W/mK or higher, about 0.55 W/mK or higher, or about 0.6 W/mK or higher. A thermal conductivity of the cured product of the epoxy resin composition in the electronic device may be, for example, in a range of about 0.4 W/mK to about 50 W/mK, about 0.45 W/mK to about 45 W/mK, about 0.5 W/mK to about 40 W/mK, about 0.55 W/mK to about 30 W/mK, about 0.55 W/mK to about 20 W/mK, about 0.55 W/mK to about 10 W/mK, or about 0.6 W/mK to about 10 W/mK. When a thermal conductivity of at least one of the cured product, sealing portion, substrate portion, reinforcement portion, or attachment portion in the electronic device is within these ranges, thermal stability of the electronic device may further be improved.

Figure 4:
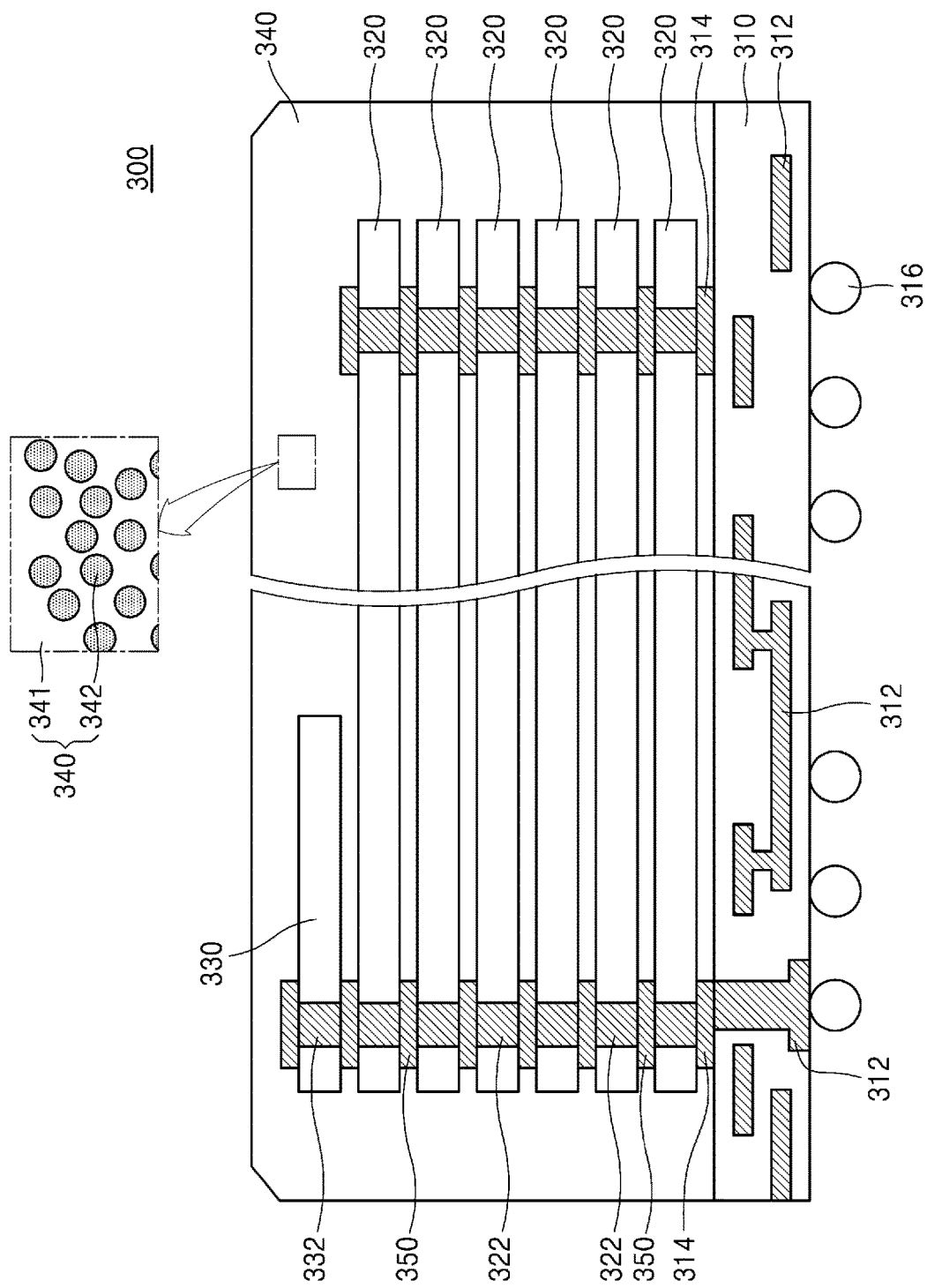
FIG. 4 is a schematic cross-sectional view of an electronic device according to an embodiment.
Figure 5:
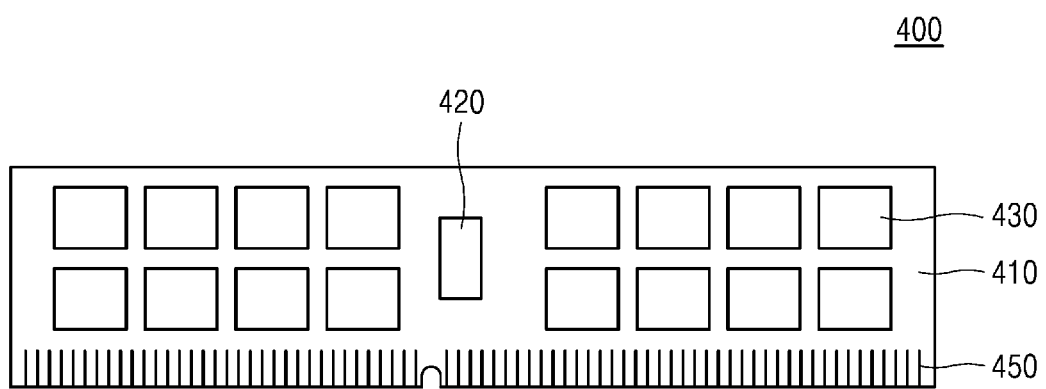
FIG. 5 is a schematic cross-sectional view of an electronic device according to an embodiment.

The electronic device may be, for example, an electronic control unit, a sensor, a sensor module, a camera, a camera module, a module with an indicator, a module with a battery, or a module with a coin battery in which a substrate having electronic compartments mounted thereon is encapsulated. The electronic device may be, for example, an integrated circuit device having electronic components mounted thereon or a printed circuit board having electronic components mounted thereon. Referring to FIG. 4, an integrated circuit device 300 includes a plurality of semiconductor chips 320 sequentially stacked on a package substrate 310. A control chip 330 is connected on the plurality of semiconductor chips 320. A stack of the plurality of semiconductor chips 320 and the control chip 330 is sealed on the package substrate 310 by a molding portion 340. The molding portion 340 may have similar features with the molding portion 110 in FIG. 3. The molding portion 340 may be prepared using the epoxy resin composition described herein. The molding portion 340 includes an epoxy resin 341 and a plurality of fillers 342 dispersed in the epoxy resin 341. Details about the epoxy resin 341 and the fillers 342 may be the same with those of the epoxy resin 1 and the fillers 2 in FIG. 3. FIG. 4 shows an example structure in which the plurality of semiconductor chips 320 are vertically stacked. The plurality of semiconductor chips 320 may be arranged in a horizontal direction on the package substrate 310 or may be arranged in a combined structure of a vertical direction mounting and a horizontal direction mounting. The control chip 330 may be omitted. The package substrate 310 may be a flexible printed circuit board, a rigid printed circuit board, or a combination thereof. The package substrate 310 includes substrate internal distribution lines 312 and coupling terminals 314. The coupling terminals 314 may be formed on a surface of the package substrate 310. Solder balls 316 are formed on the other surface of the package substrate 310. The coupling terminals 314 are electrically connected to the solder balls 316 via the substrate internal distribution lines 312. The solder balls 316 may be replaced by conductive bumps or lead grid array (LGA). The plurality of semiconductor chips 320 and the control chip 330 may respectively include coupling structures 322 and 332. The coupling structures 322 and 332 may each be formed of, for example, a through silicon via (TSV) contact structure. The coupling structures 322 and 332 in the plurality of semiconductor chips 320 and the control chip 330 are electrically connected to the coupling terminals 314 of the package substrate 310 via coupling portions 350 such as bumps. The plurality of semiconductor chips 320 may each include system LSI, flash memory, DRAM, SRAM, EEPROM, PRAM, MRAM, or RRAM. The control chip 330 may include logic circuits such as a serializer/deserializer (SER/DES) circuit. Referring to FIG. 5, an integrated circuit device 400 includes a module substrate 410; and a control chip 420 and a plurality of semiconductor packages 430 mounted on the module substrate 410. A plurality of input/output terminals 450 are formed on the module substrate 410. The plurality of semiconductor package 430 includes at least one of the semiconductor package 100 of FIG. 3 or the integrated circuit device 300 of FIG. 4.

Article

According to an embodiment, an article includes a substrate; and a cured product of an epoxy resin composition including a curing agent and an epoxy compound including a 5-membered aromatic heterocyclic ring and represented by Formula 1, an epoxy compound including a 5-membered aromatic heterocyclic ring and represented by Formula 2, or a combination thereof, a sealing portion including the cured product of the epoxy resin composition, a substrate portion including the cured product of the epoxy resin composition, a reinforcement portion including the cured product of the epoxy resin composition, or an attachment portion including the cured product of the epoxy resin composition. When the article includes at least one of the cured product, sealing portion, substrate portion, reinforcement portion, or attachment portion, heat release characteristics of the article may be improved, and as a result, thermal stability of the article may be improved.

A thermal conductivity of the cured product of the epoxy resin composition in the article may be, for example, about 0.4 W/mK or higher, about 0.45 W/mK or higher, about 0.5 W/mK or higher, about 0.55 W/mK or higher, or about 0.6 W/mK or higher. A thermal conductivity of the cured product of the epoxy resin composition in the article may be, for example, in a range of about 0.4 W/mK to about 50 W/mK, about 0.45 W/mK to about 45 W/mK, about 0.5 W/mK to about 40 W/mK, about 0.55 W/mK to about 30 W/mK, about 0.55 W/mK to about 20 W/mK, about 0.55 W/mK to about 10 W/mK, or about 0.6 W/mK to about 10 W/mK. When a thermal conductivity of at least one of the cured product, sealing portion, substrate portion, reinforcement portion, and attachment portion in the article is within these ranges, thermal stability of the article may further be improved.

The article may be, for example, an MP3 player, a navigation system, a portable multimedia player (PMP), a solid state disk (SSD), or a household appliance, but embodiments are not limited thereto.

According to an embodiment, a method of preparing an article includes providing the epoxy resin composition described herein on a substrate; and curing the epoxy resin composition.

The epoxy resin composition may be provided in various state such as a liquid state, a solid state, and a semi-cured state on the substrate. The epoxy resin composition provided in a liquid state may be provided in a molten state or a state dissolved in a solvent. The epoxy resin composition provided in a solid state may be provided in various shapes such as a powdery shape, a granular shape, or a sheet shape on the substrate. The epoxy resin composition may be provided in a state not cured at all, partially cured, or in a semi-cured state on the substrate. The epoxy resin composition may be molded into a predetermined shape after being provided on the substrate or may be provided on the substrate after being molded into a predetermined shape.

Once the epoxy resin composition is provided on the substrate, the epoxy resin composition may be cured to prepare an article. The cured epoxy resin composition may form a sealing portion, a substrate portion, a reinforcement portion, or an attachment portion of the article, but embodiments are not limited thereto.

A method of curing the epoxy resin composition may include thermal curing or ultraviolet light curing, but embodiments are not limited thereto. The epoxy resin composition may be cured by heat. A curing temperature of the epoxy resin composition may be about 100° C. or higher, about 110° C. or higher, or about 120° C. or higher. A curing temperature of the epoxy resin composition may be, for example, about 200° C. or lower, about 195° C. or lower, about 190° C. or lower, about 185° C. or lower, or about 180° C. or lower. A curing temperature of the epoxy resin composition may be, for example, in a range of about 100° C. to about 200° C., about 110° C. to about 200° C., about 120° C. to about 200° C., about 130° C. to about 200° C., about 150° C. to about 195° C., about 160° C. to about 190° C., about 150° C. to about 185° C., or about 150° C. to about 180° C. When the epoxy resin composition is cured at a curing temperature within these ranges, damages caused by thermal deformation of a semiconductor or electronic components may be prevented.

Hereinafter, definitions of substituents used in the formulae of the present specification are the same as follows.

As used herein, substituents of a substituted alkyl group, a substituted alkylene group, a substituted alkenylene group, a substituted alkynylene group, and a substituted alkadienylene group may be each independently a halogen atom, a hydroxyl group, a C1 to C5 alkyl group, a C1 to C5 alkoxy group, a C1 to C5 alkylthio group, a C6-C30 aryloxy group, a C6-C30 arylthio group, or a combination thereof.

As used herein, the term "alkyl" refers to a fully saturated branched or unbranched (straight chain or linear) hydrocarbon group.

Example of the alkyl group are a methyl group, an ethyl group, an i-propyl group, an isopropyl group, an i-butyl group, an isobutyl group, a sec-butyl group, an i-pentyl group, an isopentyl group, a neopentyl group, an i-hexyl group, a 3-methylhexyl group, a 2,2-dimethylpentyl group, a 2,3-dimethylpentyl group, and an i-heptyl group.

At least one hydrogen atom of the alkyl group may be substituted with a substituent a halogen atom, a hydroxyl group, an alkoxy group, a nitro group, a cyano group, an amino group, an amidino group, a hydrazine, a hydrazone, a carboxyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C30 alkylthio group, a C6-C30 aryloxy group, a C6-C30 arylthio group, a C1 to C20 heteroalkyl group, a C3 to C20 heterocyclo alkyl group, or a combination thereof.

As used herein, the term "alkenyl group" refers to an alkyl group including at least one carbon-carbon double bond.

As used herein, the term "alkynyl group" refers to an alkyl group including at least one carbon-carbon triple bond.

As used herein, the term "alkadienyl group" refers to an alkyl group including two carbon-carbon double bonds.

Examples of "a halogen atom" include fluorine, bromine, chlorine, and iodine.

As used herein, the term "alkoxy" refers to "alkyl-O—", where the alkyl is the same as defined above. Examples of the alkoxy group may include a methoxy group, an ethoxy group, a propoxy group, a 2-propoxy group, a butoxy group, a tert-butoxy group, a pentyloxy group, a hexyloxy group, a cyclopropoxy group, and a cyclohexyloxy group. At least one hydrogen atom in the alkoxy group may be substituted with the same substituent as described above in connection with the alkyl group.

As used herein, the term "alkylthio" refers to "alkyl-S—", where the alkyl is the same as defined above. Examples of the alkylthio group may include a methylthio group, a ethylthio group, a propylthio group, a isopropylthio group, a butylthio group, a tert-butylthio group, a pentylthio group, a hexylthio group, a cyclopropylthio group, and a cyclohexylthio group. At least one hydrogen atom in the alkylthio group may be substituted with the same substituent as described above in connection with the alkyl group.

As used herein, the term "aryl" is used alone or in combination, and refers to an aromatic hydrocarbon group having one or more rings. The term "aryl" covers a group in which an aromatic ring is fused to one or more cycloalkyl rings. Examples of the aryl group may include a phenyl group, a naphthyl group, or a tetrahydronaphthyl group. At least one hydrogen atom of the aryl group may be substituted with the same substituent as described above in connection with the alkyl group.

The term "aryloxy" used herein refers to aryl-O—, where the aryl is the same as defined above. Non-limiting examples of the aryloxy group may include a phenoxy group, a naphthoxy group, or a tetrahydronaphthyloxy group. At least one hydrogen atom of the "aryloxy" group may be substituted with the same substituent as described above in connection with the alkyl group.

The "arylthio" used herein refers to aryl-S—, where the aryl is the same as defined above. Non-limiting examples of the arylthio group may include a phenylthio group, a naphthylthio group, or a tetrahydronaphthylthio group. At least one hydrogen atom of the "arylthio" group may be substituted with the same substituent as described above in connection with the alkyl group.

Also, as used herein, when a definition is not otherwise provided, 'hetero' may refer to one including 1 to 4 heteroatoms selected from I, O, S, Se, Te, Si, or P.

As used herein, when a linking group Ln (e.g., n may be an integer of 1 to 12) is defined to be —C(=O)O—, it means that Ln may be —C(=O)O— or —OC(=O)—. The same applies to —(CH$_2$)$_2$—C(=O)—, —CH=CH—C(=O)—, —CH=N—, —NH—C(=O)O—, —C(=O)—NH—, and —OC(=O)—NH—S(=O)O—. Take —(CH$_2$)$_2$—C(=O)— for example, when Ln is defined to be —(CH$_2$)$_2$—C(=O)—, it means that Ln may be —(CH$_2$)$_2$—C(=O)— or —C(=O)—(CH$_2$)$_2$—.

As used herein, the term "heteroaryl" refers to an aryl group, in which at least one carbon atom or CH is substituted with a heteroatom or a chemical group containing at least one heteroatom.

As used herein, the term "alkylene group" refers to a bivalent aliphatic hydrocarbon group corresponding to an "alkyl" group.

As used herein, the term "alkenylene group" refers to a bivalent aliphatic hydrocarbon group corresponding to an "alkenyl" group.

As used herein, the term "alkynylene group" refers to a bivalent aliphatic hydrocarbon group corresponding to an "alkynyl" group.

As used herein, the term "alkadienylene group" refers to a bivalent aliphatic hydrocarbon group corresponding to an "alkadienyl" group.

As used herein, the term "arylene group" refers to a bivalent aromatic hydrocarbon group corresponding to an "aryl" group.

As used herein, the term "heteroarylene group" refers to a bivalent aryl group in which at least one carbon atom or CH is substituted with a heteroatom or a chemical group containing at least one heteroatom.

As used herein, the open ended "—" refers to a single bond or a methyl group, for example, in the following structures "—" without any R substituent refers to a single bond or a methyl group. The open ended "—" in a group refers to a single bond.

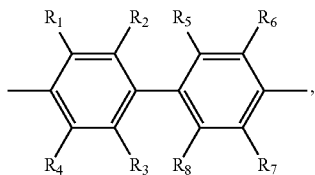

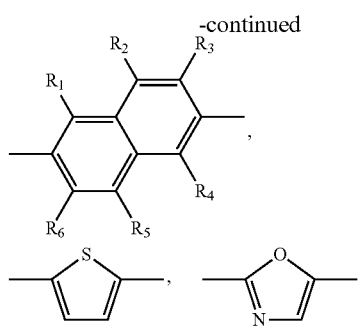

The term "room temperature" used herein refers to a temperature of about 25° C.

One or more embodiments will now be described in more detail with reference to the following examples. However, these examples are not intended to limit the scope of the one or more embodiments. The wording "'B' was used instead of 'A'" used in describing Synthesis Examples means that an amount of 'A' used was identical to an amount of 'B' used, in terms of a molar equivalent.

EXAMPLES

Preparation of Epoxy Compound and Cured Product

Example 1

Preparation of Epoxy Compound 16 gram (g) of 2,5-furandicarboxylic acid (FDA), 100 milliliter (ml) of tetrahydrofuran (THF), and 0.05 ml of dimethylformamide (DMF) were added to a 500 ml glass reactor, 20 g of oxalyl chloride was added thereto, the resulting mixture was allowed to be reacted at room temperature for 2 hours, and thus furan-2,5-dicarbonyl dichloride (FDCDCl) was obtained. After dissolving 9 g of hydroquinone in 100 ml of pyridine, 8 g of FDCDCl was added thereto and allowed to be reacted at room temperature for 4 hours. Water was added to the resulting solution, and a precipitate was obtained through filtration. The precipitate was washed with water several times, recrystallized in pyridine, and dried in a vacuum oven at 60° C. for 12 hours to prepare Intermediate 1-1.

Intermediate 1-1

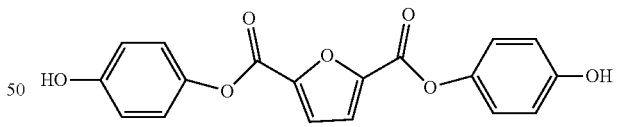

5 g of Intermediate 1-1, 50 g of epichlorohydrin, and 20 g of isopropyl alcohol were added to a 250 ml reactor. Once the inside of the reactor was sufficiently replaced with nitrogen gas, a temperature in the reactor was increased to 50° C. under a flow of nitrogen gas, and the contents of the reactor were refluxed for 5 hours while maintaining the temperature in the reactor at 50° C. The temperature in the reactor was decreased to room temperature, and 1.2 g of sodium hydroxide (NaOH) (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using CH$_2$Cl$_2$/CH$_3$OH, and thus a compound represented by Formula 11a was prepared.

Formula 11a

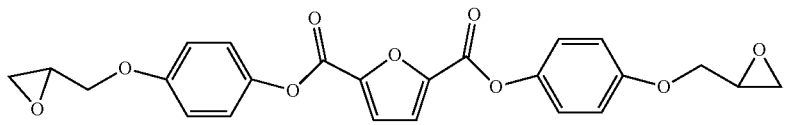

$^1$H NMR (500 MHz, CDCl$_3$): δ 7.5 (s, 2H), 7.2 (d, 4H), 6.9-6.8 (d, 4H), 4.2-3.9 (m, 4H), 3.0 (m, 2H), 2.9 (s, 2H), 2.8-2.4 (m, 4H).

Preparation of Cured Product

The prepared epoxy compound represented by Formula 11a and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Example 2

Preparation of Epoxy Compound 10 g of 1H-pyrrole-2,5-diol, 20 g of hydroquinone, 3 g of p-toluenesulfonic acid, and 200 ml of 1,2-dichlorobenzene were added to a 500 ml glass reactor and were allowed to react under a flow of nitrogen gas at 160° C. for 4 hours. Water was added to the resulting solution, and a precipitate was obtained through filtration. The precipitate was washed with water several times and dried in a vacuum oven at 60° C. for 12 hours to prepare Intermediate 2-1.

Intermediate 2-1

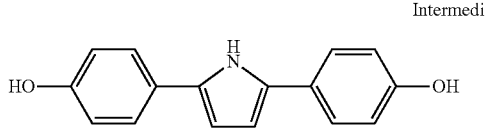

5 g of Intermediate 2-1, 50 g of epichlorohydrin, and 20 g of isopropyl alcohol were added to a 250 ml reactor. Once the inside of the reactor was sufficiently replaced with nitrogen gas, a temperature in the reactor was increased to a temperature of 50° C. under a flow of nitrogen gas, and the contents of the reactor were refluxed for 5 hours while maintaining the temperature in the reactor at 50° C. The temperature in the reactor was decreased to room temperature, and 1.2 g of NaOH (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using CH$_2$Cl$_2$/CH$_3$OH, and thus a compound represented by Formula 10c was prepared.

Formula 10c

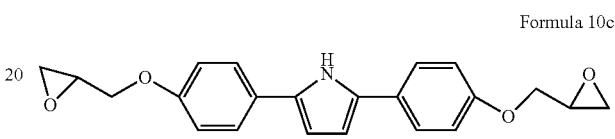

$^1$H NMR (500 MHz, CDCl$_3$): δ 11.9 (s, 1H), 7.9 (d, 4H), 7.1 (d, 4H), 4.2-3.9 (m, 4H), 3.0 (m, 2H), 2.6-2.4 (m, 4H)

Preparation of Cured Product

The prepared epoxy compound represented by Formula 10c and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Example 3

Preparation of Epoxy Compound 200 ml of 95% ethanol, 170 g of Intermediate 1-1 prepared in Example 1, 0.09 g of sodium hydrosulfite, and 21 g of 1,4-dibromobutane were added to a 1 liter (L) glass reactor, and the contents were mixed. Then, while stirring and refluxing the mixture for 1 hour, 8.4 g of potassium hydroxide (KOH) was dissolved in 100 ml of 95% ethanol and slowly added to the reactor, and the content was refluxed for 8 hours. The solution was cooled to room temperature and neutralized using 30 weight percent (wt %) sulfuric acid, and 500 ml of 95% ethanol was added thereto. A precipitate was obtained through filtration. The precipitate was washed with ethanol several times and vacuum-dried to prepare Intermediate 1-2.

Intermediate 1-2

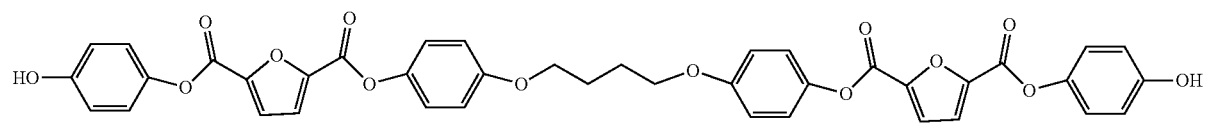

30 g of Intermediate 1-2, 148 g of epichlorohydrin, and 80 g of isopropyl alcohol were added to a 500 ml reactor. Once the inside of the reactor was sufficiently replaced with nitrogen gas, a temperature in the reactor was increased to a temperature of 50° C. under a flow of nitrogen gas, and the contents of the reactor were refluxed for 5 hours while maintaining the temperature in the reactor at 50° C. The temperature in the reactor was decreased to room temperature, and 3.2 g of NaOH (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using $CH_2Cl_2$/$CH_3OH$, and thus a compound represented by Formula 13a was prepared.

Formula 13a

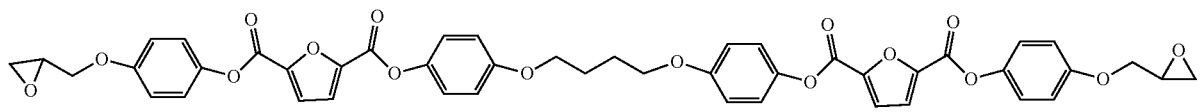

$^1$H NMR (500 MHz, CDCl$_3$): δ 7.8 (s, 4H), 7.1 (d, 8H), 6.9 (d, 8H), 4.2-4.1 (m, 6H), 3.04 (m, 2H), 2.6-2.4 (m, 4H), 1.9 (m, 4H)

Preparation of Cured Product

The prepared epoxy compound represented by Formula 13a and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Example 4

Preparation of Epoxy Compound 200 ml of 95% ethanol, 170 g of Intermediate 2-1 prepared in Example 2, 0.09 g of sodium hydrosulfite, and 21 g of 1,4-dibromobutane were added to a 1 L glass reactor, and the contents were mixed. Then, while stirring and refluxing the mixture for 1 hour, 8.4 g of potassium hydroxide was dissolved in 100 ml of 95% ethanol and slowly added to the reactor, and the content was refluxed for 8 hours. The solution was cooled to room temperature and neutralized using 30 wt % sulfuric acid, and 500 ml of 95% ethanol was added thereto. A precipitate was obtained through filtration. The precipitate was washed with ethanol several times and vacuum-dried to prepare Intermediate 2-2.

Intermediate 2-2

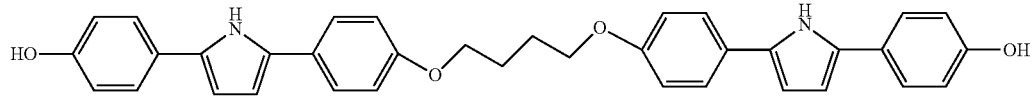

30 g of Intermediate 2-2, 148 g of epichlorohydrin, and 80 g of isopropyl alcohol were added to a 500 ml reactor. Once the inside of the reactor was sufficiently replaced with nitrogen gas, a temperature in the reactor was increased to a temperature of 50° C. under a flow of nitrogen gas, and the contents of the reactor were refluxed for 5 hours while maintaining the temperature in the reactor at 50° C. The temperature in the reactor was decreased to room temperature, and 3.2 g of NaOH (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using $CH_2Cl_2$/$CH_3OH$, and thus a compound represented by Formula 12c was prepared.

Formula 12c

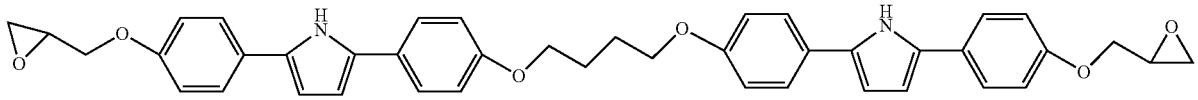

¹H NMR (500 MHz, CDCl₃): δ 12.0 (s, 2H), 7.9 (d, 8H), 7.1 (d, 8H), 6.5 (s, 4H), 4.2-4.1 (m, 6H), 3.9 (m, 2H), 3.0 (m, 2H), 2.6 (m, 2H), 2.3 (m, 2H), 1.9 (m, 4H)

Preparation of Cured Product

The prepared epoxy compound represented by Formula 12c and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Example 5

Preparation of Epoxy Compound 20.0 g of 3-(2-trimethylsilylethynyl)phenol and 150 ml of DMF were added to a 500 ml glass reactor and mixed at room temperature under a flow of nitrogen gas, and 85 g of 3-azidophenol, 0.1 g of copper bromide (CuBr), and 0.2 g of 2,2-bipyridyl were further added thereto, and allowed to react at 80° C. for 24 hours. The thus obtained solution was cooled to room temperature, water and 1 L of ethyl acetate were added to wash an organic mixture layer, and the layer was dried using anhydrous MgSO₄. A solvent from the dried solution was removed through vacuum distillation, and a precipitate obtained therefrom was recrystallized using acetic acid/water to prepare Intermediate 3-1.

Intermediate 3-1

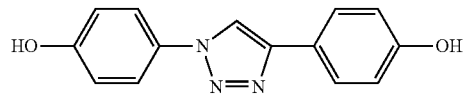

200 ml of 95% ethanol, 180 g of Intermediate 3-1, 0.09 g of sodium hydrosulfite, and 21 g of 1,4-dibromobutane were added to a 1 L glass reactor, and the contents were mixed. Then, while stirring and refluxing the mixture for 1 hour, 8.4 g of potassium hydroxide was dissolved in 100 ml of 95% ethanol and slowly added to the reactor, and the content was refluxed for 8 hours. The solution was cooled to room temperature and neutralized using 30 wt % sulfuric acid, and 500 ml of 95% ethanol was added thereto. A precipitate was obtained through filtration. The precipitate was washed with ethanol several times and vacuum-dried to prepare Intermediate 3-2.

Intermediate 3-2

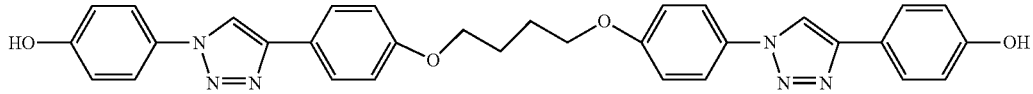

30 g of Intermediate 3-2, 148 g of epichlorohydrin, and 80 g of isopropyl alcohol were added to a 500 ml reactor. Once the inside of the reactor was sufficiently replaced with nitrogen gas, a temperature in the reactor was increased to a temperature of 50° C. under a flow of nitrogen gas, and the contents of the reactor were refluxed for 5 hours while maintaining the temperature in the reactor at 50° C. The temperature in the reactor was decreased to room temperature, and 3.2 g of NaOH (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using CH₂Cl₂/CH₃OH, and thus a compound represented by Formula 12l was prepared.

Formula 12l

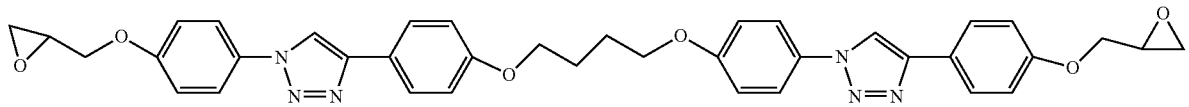

$^1$H NMR (500 MHz, CDCl$_3$): δ 8.1 (s, 2H), 7.6 (d, 4H), 7.5 (d, 4H), 7.1 (d, 4H), 4.2 (m, 2H), 4.1 (m, 4H), 3.9 (m, 2H), 3.0 (m, 2H), 2.6 (m, 2H), 2.4 (m, 2H), 1.9 (m, 4H)

Preparation of Cured Product

The prepared epoxy compound represented by Formula 121 and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Comparative Example 1

Preparation of Epoxy Compound

A phenol aralkyl type epoxy resin, NC3000 (available from Nippon Kayaku Co., Ltd.), represented by Formula A was purchased and used as received.

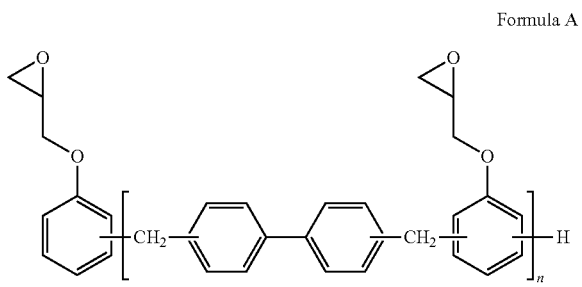

Formula A

Preparation of Cured Product

The prepared epoxy compound represented by Formula A and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Comparative Example 2

Preparation of Epoxy Compound

An epoxy compound, SH400E (available from DIC Inc., Japan), represented by Formula B was purchased and used as received.

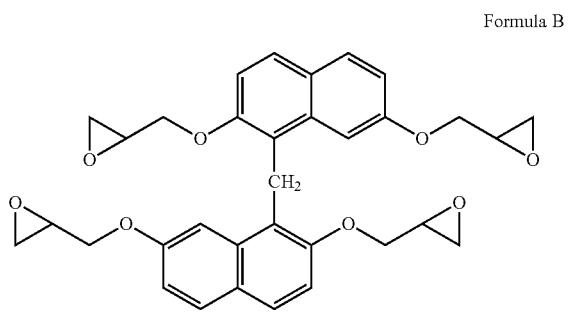 [SMILES: c1cc2ccc(OCC3CO3)c(Cc3c(OCC4CO4)ccc4ccc(OCC5CO5)cc34)c2cc1OCC1CO1]

Formula B

Preparation of Cured Product

The prepared epoxy compound represented by Formula B and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Comparative Example 3

Preparation of Epoxy Compound

An epoxy compound, TMBO(H) (available from Hitachi Chemical), represented by Formula C was purchased and used as received.

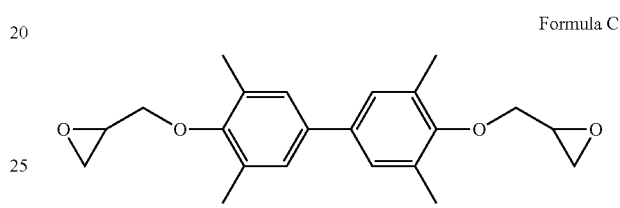

Formula C

Preparation of Cured Product

The prepared epoxy compound represented by Formula C and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Comparative Example 4

Preparation of Epoxy Compound

An epoxy compound represented by Formula D was synthesized as in the following method and used.

75 g of hydroquinone, 35 g of 4-hydrobenzoic acid, 0.5 g of p-toluene sulphonic acid, and 300 ml of 1,2-dichlorobenzene were added to a 500 ml glass reactor and mixed under a flow of nitrogen gas, and the contents were allowed to react at 160° C. for 4 hours. Water was added to the resulting solution, and a precipitate was obtained through filtration. The precipitate was washed with water several times, recrystallized using methanol/water, and dried in a vacuum oven at 60° C. for 12 hours to prepare Intermediate 4-1.

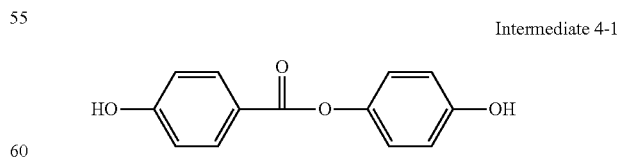

Intermediate 4-1

5 g of Intermediate 4-1, 50 g of epichlorohydrin, and 20 g of isopropyl alcohol were added in a 250 ml reactor. Once the inside of the reactor was sufficiently replaced with nitrogen gas, a temperature in the reactor was increased to a temperature of 50° C. under a flow of nitrogen gas, and the contents of the reactor were refluxed for 5 hours while maintaining the temperature in the reactor at 50° C. The temperature in the reactor was decreased to room temperature, and 1.2 g of NaOH (25% aqueous solution) was added dropwise to the reactor over the course of 1 hour. The temperature of the reactor was increased to 60° C., and the content in the reactor was stirred for 4 hours. The temperature of the reactor was decreased to room temperature, the contents of the reactor were recrystallized using $CH_2Cl_2$/$CH_3OH$, and thus a compound represented by Formula D was prepared.

Formula D

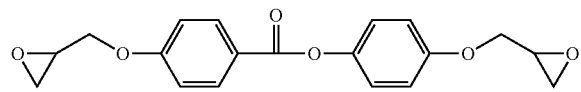

Preparation of Cured Product

The prepared epoxy compound represented by Formula D and a phenol-based curing agent, MEH7500 (polyfunctional phenol, available from Meiwa Plastic Industries, Ltd.), were mixed at an equivalent ratio of 1:1 to prepare an epoxy resin composition.

5 g of the prepared epoxy resin composition was added to an aluminum mold and cured by increasing a temperature of the composition to 190° C., and thus a cured product of the epoxy resin composition was prepared as a sample.

Evaluation Example 1: Measurement of Thermal Conductivity

Thermal conductivities of the samples, which are the cured products of the epoxy resin compositions including a curing agent and the epoxy compounds each respectively prepared in Examples 1 to 5 and Comparative Examples 1 to 4, were measured. The results of the measurement are shown in Table 1.

The heat conductivities were evaluated by a modified transient plane source (MTPS) method using the C-THERM TCI™ thermal conductivity analyzer.

TABLE 1

Thermal conductivities of the samples

| | Thermal conductivity [W/mK] |
|---|---|
| Example 1 | 0.51 |
| Example 2 | 0.54 |
| Example 3 | 0.59 |
| Example 4 | 0.60 |
| Example 5 | 0.61 |
| Comparative Example 1 | 0.21 |
| Comparative Example 2 | 0.27 |
| Comparative Example 3 | 0.33 |
| Comparative Example 4 | 0.31 |

As shown in Table 1, thermal conductivities of the cured products obtained from the epoxy compounds of Examples 1 to 4 increased about 50% or higher, compared to those of the cured products obtained from the epoxy compounds of Comparative Examples 1 to 4.

Also, the thermal conductivities of the cured products obtained from the epoxy compound of Examples 3 to 5 increased about 10% or higher, compared to those of the cured products obtained from the epoxy compounds of Examples 1 and 2.

As described above, according to an aspect of one or more embodiments, a cured product of an epoxy resin composition including an epoxy compound having a 5-membered aromatic heterocyclic ring may have an improved thermal conductivity, and a semiconductor device including the cured product, an electronic device including the cure product, and an article including the cured product may have improved thermal stability.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present detailed description as defined by the following claims.

What is claimed is:

1. An epoxy compound having a 5-membered aromatic heterocyclic ring represented by Formula 2:

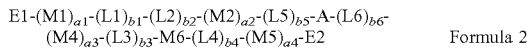

Formula 2 wherein, in Formula 2,

M1, M2, M4, and M5 are each independently an arylene group represented by Formulae 3a to 3e,

Formula 3a

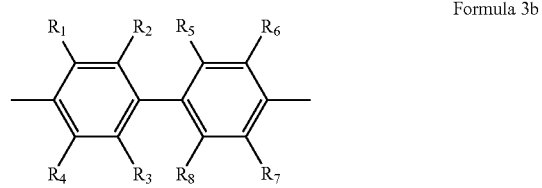

Formula 3b

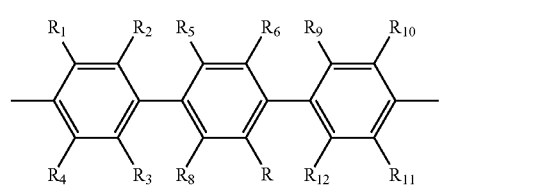

Formula 3c

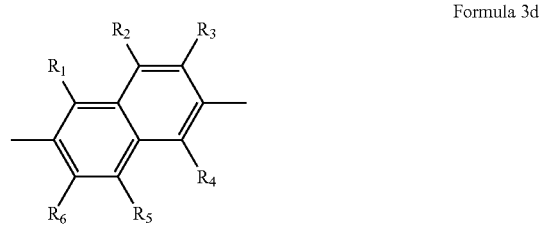

Formula 3d

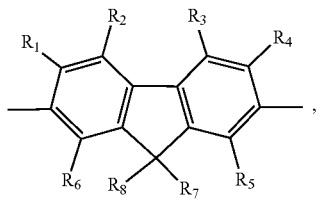

wherein, in Formulae 3a to 3e, $R_1$, $R_2$, $R_3$, $R_4$, $R_5$, $R_6$, $R_7$, $R_8$, $R_9$, $R_{10}$, $R_{11}$, and $R_{12}$ are each independently a hydrogen, a halogen, a hydroxyl group, or a substituted or unsubstituted C1-C10 alkyl group, M3 and M6 are each independently a heteroarylene group represented by Formulae 4a to 4r,

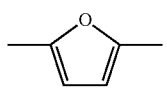 Formula 4a

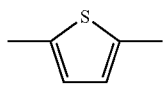 Formula 4b

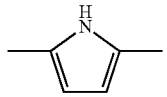 Formula 4c

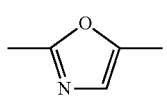 Formula 4d

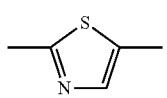 Formula 4e

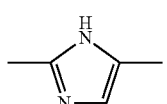 Formula 4f

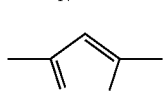 Formula 4g

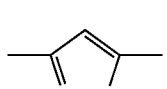 Formula 4h

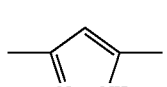 Formula 4i

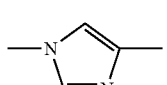 Formula 4j

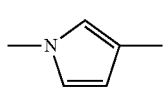 Formula 4k

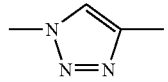 Formula 4l

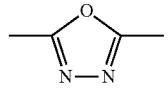 Formula 4m

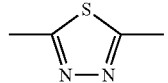 Formula 4n

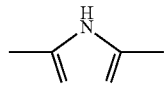 Formula 4o

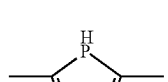 Formula 4p

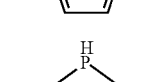 Formula 4q

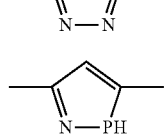 Formula 4r

L1, L2, L3, L4, L5, and L6 are each independently —O—, —S—, —C(=O)—, —S(=O)—, —C(=O)O—, —O—C(=O)O—, —(CH$_2$)$_2$—C(=O)—, —CH=CH—C(=O)—, —CH=N—, —NH—C(=O)O—, —C(=O)—NH—, or —OC(=O)—NH—S(=O)O—, A is a substituted or unsubstituted C4-C12 alkylene group, a substituted or unsubstituted C4-C12 alkenylene group, a substituted or unsubstituted C4-C12 alkynylene group, or a substituted or unsubstituted C4-C12 alkadienylene group;

E1 and E2 are each independently an epoxy-containing group, a1, a2, a3, and a4 are each independently an integer from 0 to 2, where the sum of a1 and a2 is 1 to 4, and the sum of a3 and a4 is 1 to 4, and b1, b2, b3, and b4 are each independently 0 or 1, and b5 and b6 are each independently 1 or 2.

2. The epoxy compound of claim 1, wherein the epoxy compound represented by Formula 2 is represented by one of Formulae 6a to 6f:

| | |
|---|---|
| E1-M1-L9-M3-L10-M2-L13-A1-L14-M4-L11-M6-L12-M5-E2 | Formula 6a |
| E1-M1-L9-M3-L13-A1-L14-M4-L11-M6-E2 | Formula 6b |
| E1-M3-L10-M2-L13-A1-L14-M6-L12-M5-E2 | Formula 6c |
| E1-M1-M3-M2-L13-A1-L14-M4-M6-M5-E2 | Formula 6d |
| E1-M1-M3-L13-A1-L14-M4-M6-E2 | Formula 6e |
| E1-M3-M2-L13-A1-L14-M6-M5-E2 | Formula 6f | wherein, in Formulae 6a to 6f,

M1, M2, M4 and M5 are each independently at least one arylene group represented by Formulae 3a to 3e, M3 and M6 are each independently a 5-membered ring heteroarylene group represented by Formulae 4a to 4r, L9, L10, L11, and L12 are each independently —O—, —S—, —C(=O)—, —S(=O)—, —C(=O)O—, or —O—C(=O)O—, L13 and L14 are each independently —O— or —S—, A1 is a C4-C12 alkylene group partially or fully substituted with a halogen, an unsubstituted C4-C12 alkylene group, a C4-C12 alkadienylene group partially or fully substituted with a halogen, or an unsubstituted C4-C12 alkadienylene group, and E1 and E2 are each independently an epoxy-containing group.

3. The epoxy compound of claim 2, wherein A1 is a butylene group, a pentylene group, a hexylene group, a heptylene group, an octylene group, a nonylene group, a decylene group, an undecylene group, a dodecylene group, a butadienylene group, a pentadienylene group, a hexadienylene group, a heptadienylene group, an octadienylene group, a nonadienylene group, a decadienylene group, an undecadienylene group, or a dodecadienylene group.

4. The epoxy compound of claim 1, wherein E1 and E2 are each independently an epoxy-containing group represented by Formulae 7a to 7d:

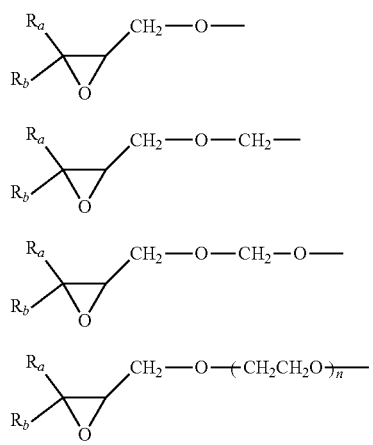

Formula 7a

Formula 7b

Formula 7c

Formula 7d wherein, in Formulae 7a to 7d, $R_a$ and $R_b$ are each independently hydrogen, a halogen, a hydroxyl group, or a substituted or unsubstituted C1-C10 alkyl group, and n is an integer from 1 to 10.

5. The epoxy compound of claim 1, wherein M1, M2, M4, and M5 are each independently at least one arylene group represented by Formulae 8a to 8e,

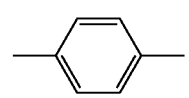

Formula 8a

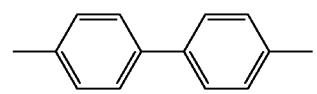

Formula 8b

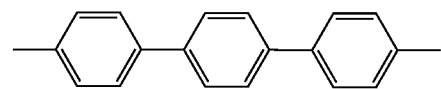

Formula 8c

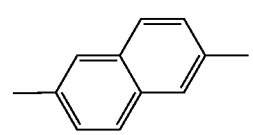

Formula 8d

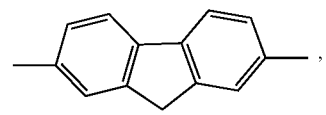

Formula 8e

E1 and E2 are each independently an epoxy-containing group represented by Formulae 9a to 9d,

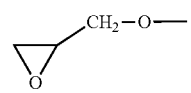

Formula 9a

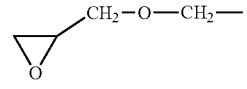

Formula 9b

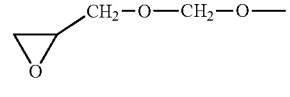

Formula 9c

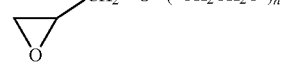

Formula 9d wherein, in Formulae 9a to 9d, n is an integer from 1 to 10.

6. The epoxy compound of claim 1, wherein the epoxy compound represented by Formula 2 is represented by one of Formulae 12a to 12r and 13a to 13r:

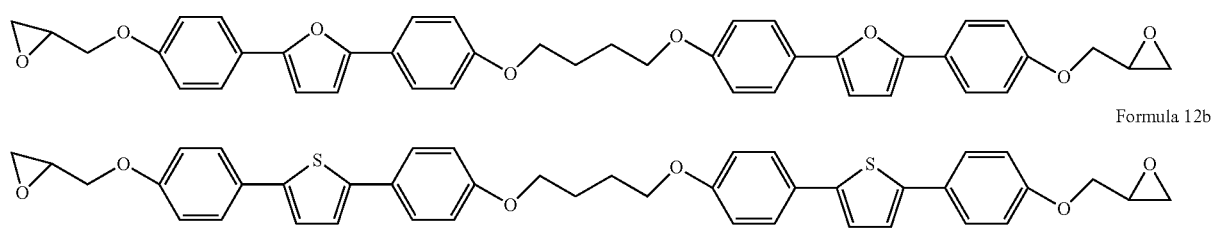

Formula 12a

Formula 12b

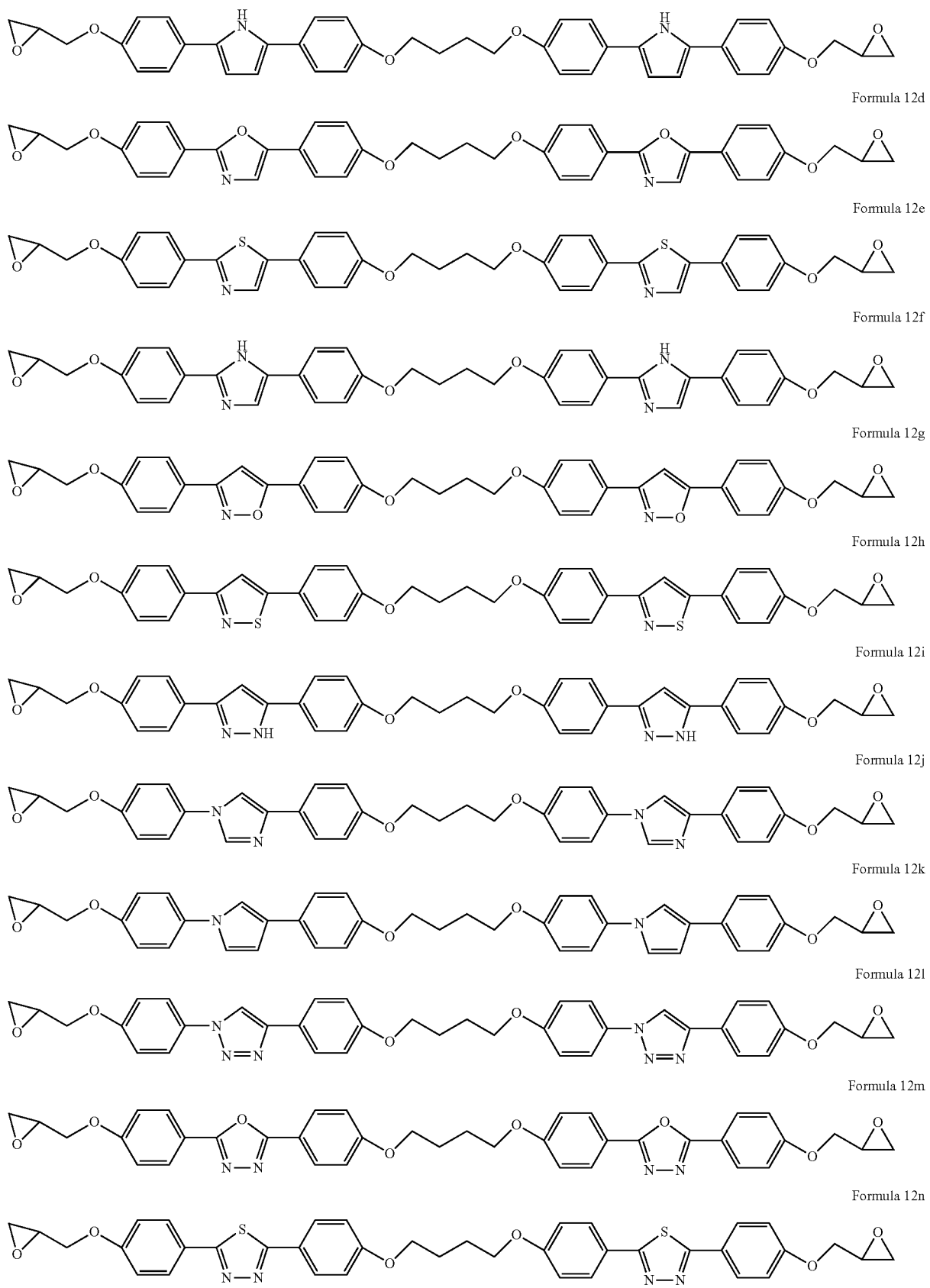

Formula 12o
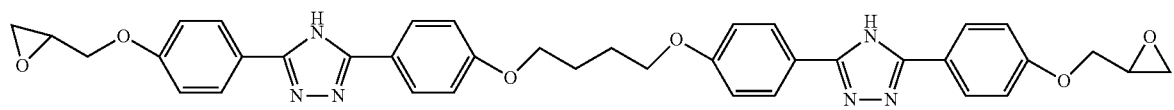
Formula 12p
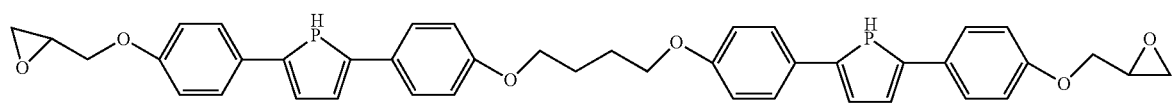
Formula 12q
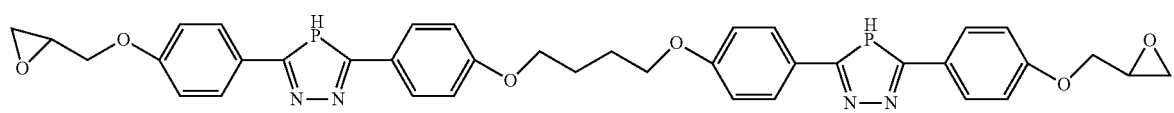
Formula 12r
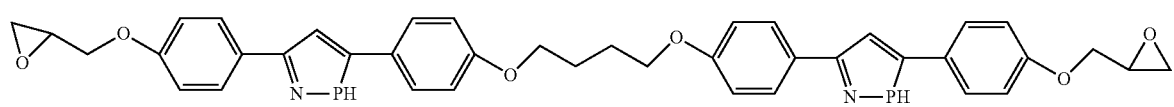
Formula 13a
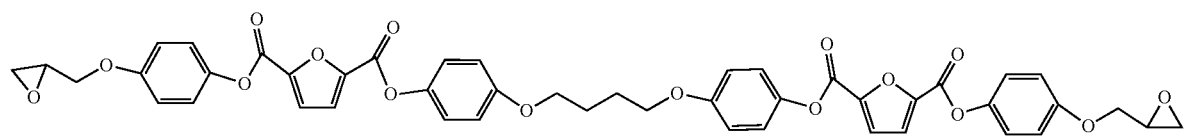
Formula 13b
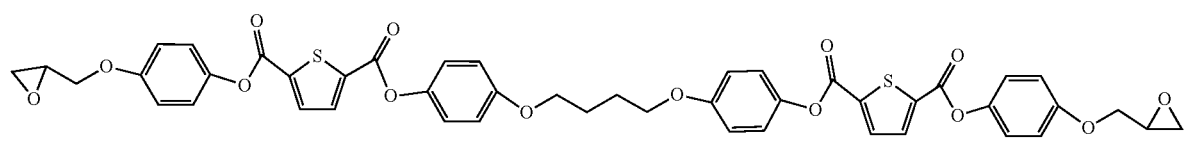
Formula 13c
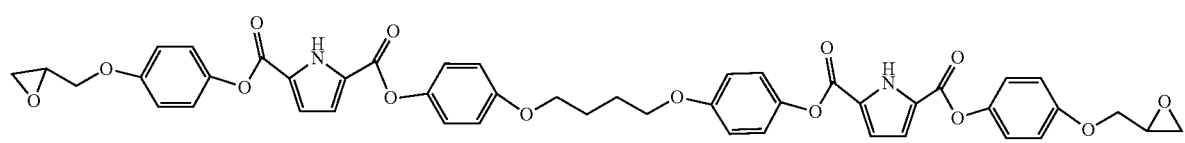
Formula 13d
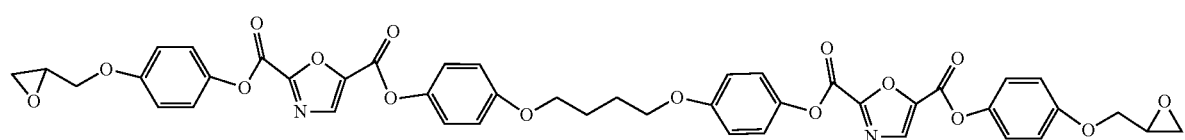
Formula 13e
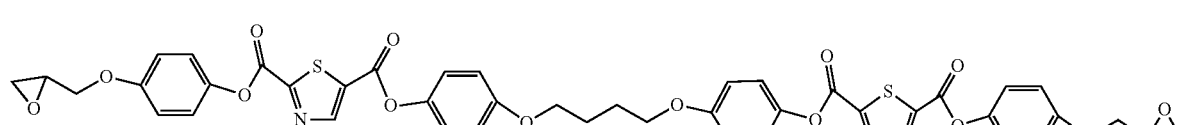
Formula 13f
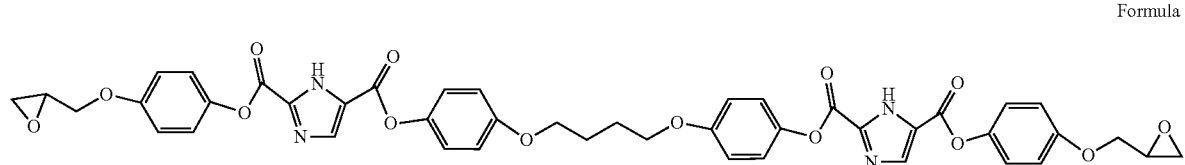

Formula 13g
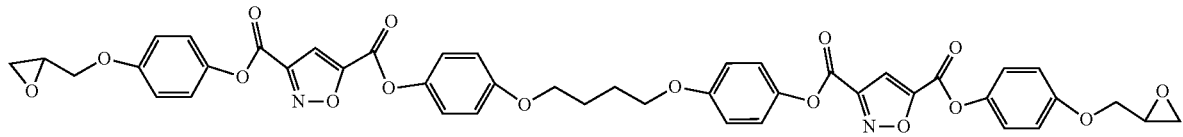
Formula 13h
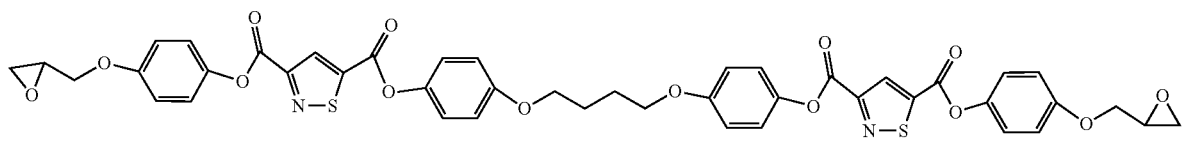
Formula 13i
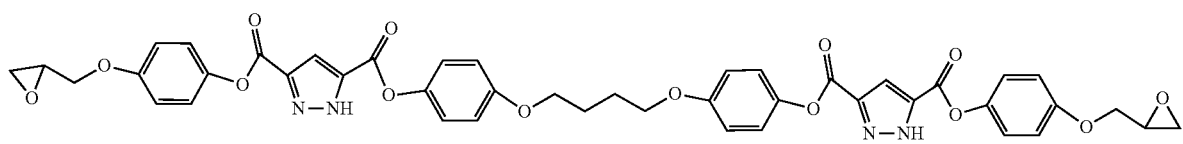
Formula 13j
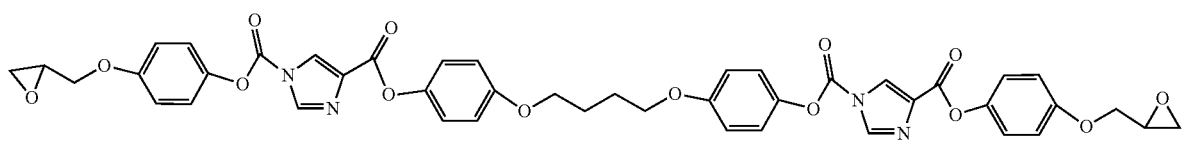
Formula 13k
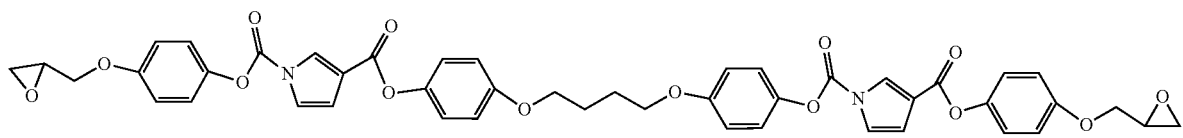
Formula 13l
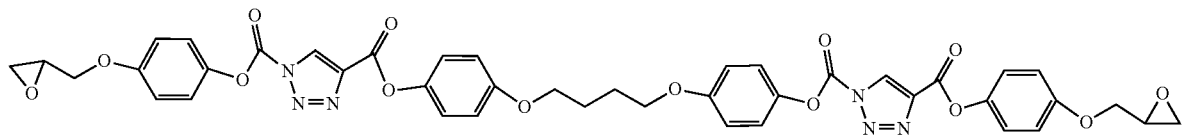
Formula 13m
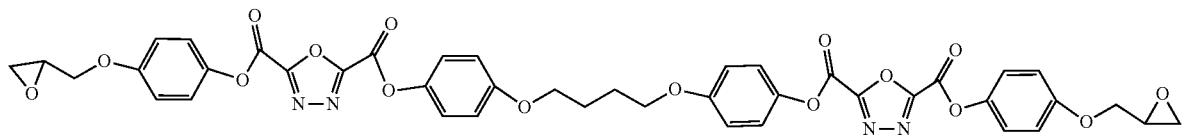
Formula 13n
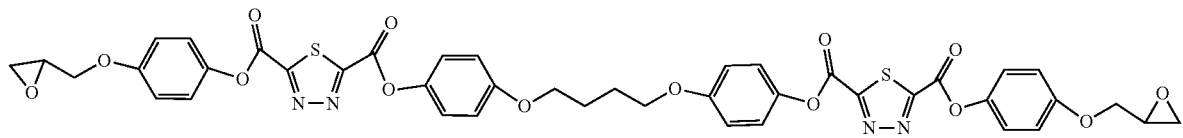
Formula 13o
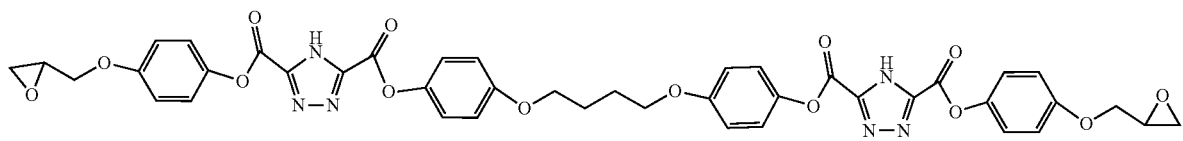

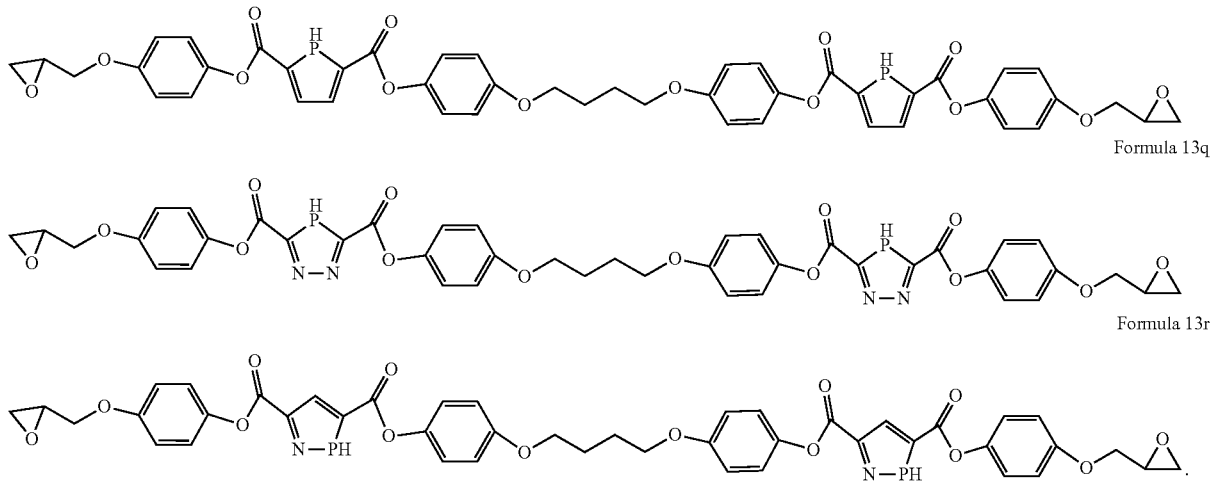

Formula 13p

Formula 13q

Formula 13r

7. The epoxy compound of claim 1, wherein a melting point of the epoxy compound represented by Formula 2 is about 30° C. to about 200° C.

8. An epoxy resin composition comprising:
the epoxy compound of claim 1; and
a curing agent.

9. The epoxy resin composition of claim 8 further comprising a filler, wherein the filler is an inorganic filler, an organic filler, or a combination thereof.

10. The epoxy resin composition of claim 9, wherein an amount of the filler is in a range of about 20 weight % to about 99 weight %, each based on the total weight of the epoxy resin composition.

11. A method of preparing an article, the method comprising:
providing the epoxy resin composition of claim 8 on a substrate; and
curing the epoxy resin composition.

12. The method of claim 11, wherein the curing of the epoxy resin composition is performed at a temperature of about 100° C. to about 200° C.

13. A semiconductor device comprising:
a substrate;
a semiconductor; and
a cured product of an epoxy resin composition comprising
a curing agent and an epoxy compound of claim 1.

14. The semiconductor device of claim 13, wherein a thermal conductivity of the cured products of the epoxy resin compositions is about 0.4 Watts per meter-Kelvin to about 50 Watts per meter-Kelvin.

15. An electronic device comprising:
a substrate;
an electronic component; and
a cured product of an epoxy resin composition comprising
a curing agent and an epoxy compound of claim 1.

16. The electronic device of claim 15, wherein a thermal conductivity of the cured product-, of the epoxy resin compositions is about 0.4 Watts per meter-Kelvin to about 50 Watts per meter-Kelvin.

17. An article comprising:
a substrate; and
a cured product of an epoxy resin composition comprising
a curing agent and an epoxy compound of claim 1.

18. The article of claim 17, wherein a thermal conductivity of the cured products of the epoxy resin compositions is about 0.4 Watts per meter-Kelvin to about 50 Watts per meter-Kelvin.

* * * * *